(12) United States Patent
Kedl et al.

(10) Patent No.: US 9,095,608 B2
(45) Date of Patent: *Aug. 4, 2015

(54) IMMUNOSTIMULATORY REGIMEN COMPRISING ADMINISTERING TYPE 1 INTERFERON AND AGONISTIC ANTI-CD40 ANTIBODY

(75) Inventors: Ross Kedl, Centennial, CO (US); Phillip J. Sanchez, Centennial, CO (US); Catherine Haluszczak, Centennial, CO (US)

(73) Assignee: The Regents of the University of Colorado, Denver, CO (US)

( * ) Notice: Subject to any disclaimer, the term of this patent is extended or adjusted under 35 U.S.C. 154(b) by 541 days.

This patent is subject to a terminal disclaimer.

(21) Appl. No.: 13/397,834

(22) Filed: Feb. 16, 2012

(65) Prior Publication Data

US 2012/0251494 A1    Oct. 4, 2012

Related U.S. Application Data

(62) Division of application No. 13/165,154, filed on Jun. 21, 2011, now Pat. No. 8,137,672, which is a division of application No. 11/743,978, filed on May 3, 2007, now Pat. No. 7,993,648.

(60) Provisional application No. 60/842,009, filed on Sep. 5, 2006, provisional application No. 60/809,821, filed on Jun. 1, 2006, provisional application No. 60/796,867, filed on May 3, 2006.

(51) Int. Cl.
| | |
|---|---|
| A61K 39/395 | (2006.01) |
| A61K 38/19 | (2006.01) |
| A61K 38/21 | (2006.01) |
| A61K 39/00 | (2006.01) |
| A61K 48/00 | (2006.01) |
| A61K 39/245 | (2006.01) |
| A61K 39/285 | (2006.01) |
| A61K 39/39 | (2006.01) |
| A61K 47/48 | (2006.01) |
| C07K 14/555 | (2006.01) |
| C07K 14/705 | (2006.01) |
| C07K 16/28 | (2006.01) |
| A61K 38/00 | (2006.01) |

(52) U.S. Cl.
CPC ............... *A61K 48/00* (2013.01); *A61K 39/245* (2013.01); *A61K 39/285* (2013.01); *A61K 39/39* (2013.01); *A61K 47/4833* (2013.01); *A61K 47/48269* (2013.01); *A61K 47/48423* (2013.01); *A61K 47/48561* (2013.01); *C07K 14/555* (2013.01); *C07K 14/70575* (2013.01); *C07K 16/2878* (2013.01); *A61K 38/00* (2013.01); *A61K 2039/505* (2013.01); *A61K 2039/55522* (2013.01); *C07K 2319/33* (2013.01); *C07K 2319/40* (2013.01); *C07K 2319/74* (2013.01); *C12N 2710/16634* (2013.01); *C12N 2710/24134* (2013.01)

(58) Field of Classification Search
None
See application file for complete search history.

(56) References Cited

U.S. PATENT DOCUMENTS

| | | |
|---|---|---|
| 5,674,492 A | 10/1997 | Armitage et al. |
| 5,677,165 A | 10/1997 | De Boer et al. |
| 5,698,679 A | 12/1997 | Nemazee |
| 5,801,227 A | 9/1998 | Fanslow et al. |
| 5,849,898 A | 12/1998 | Seed et al. |
| 5,874,082 A | 2/1999 | De Boer |
| 6,004,552 A | 12/1999 | De Boer |
| 6,017,527 A | 1/2000 | Maraskovsky et al. |
| 6,051,228 A | 4/2000 | Aruffo et al. |
| 6,056,959 A | 5/2000 | De Boer et al. |
| 6,132,978 A | 10/2000 | Gelfand |
| 6,132,992 A | 10/2000 | Ledbetter |
| 6,312,693 B1 | 11/2001 | Aruffo et al. |
| 6,315,998 B1 | 11/2001 | De Boer et al. |
| 6,410,711 B1 | 6/2002 | Armitage et al. |
| 6,413,514 B1 | 7/2002 | Aruffo et al. |
| 6,497,876 B1 | 12/2002 | Maraskovsky et al. |
| 6,653,104 B2 | 11/2003 | Goldenberg |
| 6,838,261 B1 | 1/2005 | Siegall |
| 6,843,989 B1 | 1/2005 | Siegall et al. |
| 6,946,129 B1 | 9/2005 | Siegall et al. |
| 7,063,845 B2 | 6/2006 | Mikayama et al. |

(Continued)

FOREIGN PATENT DOCUMENTS

| | | |
|---|---|---|
| WO | 2004/060319 A2 | 7/2004 |
| WO | 2005/025614 A2 | 3/2005 |

OTHER PUBLICATIONS

Santini et al., The Natural Alliance Between Type 1 and Interferon and Dendritic Cells and its Role in Linking Innate and Adaptive Immunity, Journal of Interferon & Cytokine Research, vol. 22, No. 11, (Nov. 2002), pp. 1071-1080.

(Continued)

*Primary Examiner* — Phillip Gambel
(74) *Attorney, Agent, or Firm* — Robin L. Teskin; LeClairRyan a professional Coporation

(57) ABSTRACT

A synergistic adjuvant is provided comprising synergistically effective amounts of at least one type 1 interferon and at least one CD40 agonist, wherein these moieties may be in the same or separate compositions. In addition, fusion proteins and DNA conjugates which contain a type 1 interferon/CD40 agonist/antigen combination are provided. The use of these compositions, protein and DNA conjugates as immune adjuvants for treatment of various chronic diseases such as HIV infection and for enhancing the efficacy of vaccines (prophylactic and therapeutic) is also provided.

66 Claims, 18 Drawing Sheets

(56) References Cited

U.S. PATENT DOCUMENTS

Figure 1:
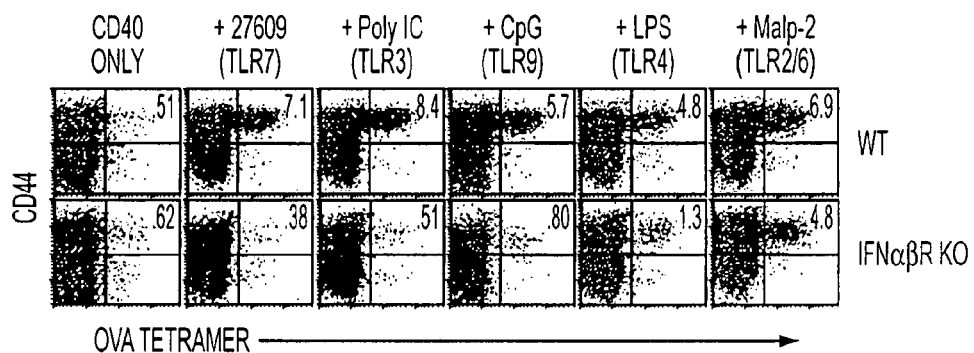

| | | |
|---|---|---|
| 7,172,759 B2 | 2/2007 | Thomas et al. |
| 7,193,064 B2 | 3/2007 | Mikayama et al. |
| 7,288,251 B2 | 10/2007 | Bedian et al. |
| 7,288,252 B2 | 10/2007 | Chu et al. |
| 7,338,660 B2 | 3/2008 | Bedian et al. |
| 7,361,345 B2 | 4/2008 | De Boer et al. |
| 7,368,106 B2 | 5/2008 | Murphy et al. |
| 7,387,271 B2 | 6/2008 | Noelle et al. |
| 7,404,950 B2 | 7/2008 | Spencer |
| 7,405,270 B2 | 7/2008 | Armitage et al. |
| 7,498,032 B2 | 3/2009 | Siegall |
| 7,510,711 B2 | 3/2009 | Siegall |
| 7,537,763 B2 | 5/2009 | Mikayama et al. |
| 7,547,438 B2 | 6/2009 | Thomas et al. |
| 7,563,442 B2 | 7/2009 | Bedian et al. |
| 7,618,633 B2 | 11/2009 | Bedian et al. |
| 7,626,012 B2 | 12/2009 | Bedian et al. |
| 7,666,422 B2 | 2/2010 | Siegall et al. |
| 7,790,166 B2 | 9/2010 | De Boer et al. |
| 7,820,170 B2 | 10/2010 | Chu et al. |
| 7,820,807 B2 | 10/2010 | Thomas et al. |
| 7,824,683 B2 | 11/2010 | Siegall et al. |
| 7,993,648 B2 | 8/2011 | Kedl et al. |
| 8,137,672 B2 * | 3/2012 | Kedl et al. ............. 424/153.1 |
| 8,361,471 B2 * | 1/2013 | Kedl et al. ............. 424/153.1 |
| 2001/0026932 A1 | 10/2001 | Thomas et al. |
| 2002/0086026 A1 | 7/2002 | Heath et al. |
| 2002/0106371 A1 | 8/2002 | De Boer |
| 2002/0142358 A1 | 10/2002 | Mikayama et al. |
| 2003/0022860 A1 | 1/2003 | Melief et al. |
| 2003/0059427 A1 | 3/2003 | Force et al. |
| 2003/0068299 A1 | 4/2003 | Murphy et al. |
| 2003/0099644 A1 | 5/2003 | Ahuja et al. |
| 2003/0118588 A1 | 6/2003 | Diehl et al. |
| 2003/0211100 A1 | 11/2003 | Bedian et al. |
| 2004/0109857 A1 | 6/2004 | Chu et al. |
| 2004/0120948 A1 | 6/2004 | Mikayama et al. |
| 2004/0141950 A1 | 7/2004 | Noelle et al. |
| 2004/0197312 A1 | 10/2004 | Moskalenko et al. |
| 2004/0235074 A1 | 11/2004 | Siegall |
| 2005/0002916 A1 | 1/2005 | Jooss et al. |
| 2005/0043517 A1 | 2/2005 | Giles-Komar |
| 2005/0136055 A1 | 6/2005 | Gladue et al. |
| 2005/0180983 A1 | 8/2005 | Keler et al. |
| 2005/0255106 A1 | 11/2005 | Diehl et al. |
| 2005/0266002 A1 | 12/2005 | Siegall |
| 2006/0062784 A1 | 3/2006 | Grant et al. |
| 2009/0081157 A1 | 3/2009 | Kornbluth et al. |

OTHER PUBLICATIONS

Loft et al. IFN-Alpha Enhances CD40 Ligand-Mediated Activation of Immature Monocyte-Derived Dendritic Cells, International Immunology, vol. 14, No. 4(2002), pp. 367-380.

Kornbluth et al., Immunostimulatory Combinations: Designing the Next Generation of Vaccine Adjuvants, Journal of Leukocyte Biology, vol. 80, No. 5 (Nov. 2006), pp. 1084-1102.

Skolnick et al., From Genes to Protein Structure and Function: Novel Applications of Computational Approaches in the Genomic Era, Trends in Biotech, 18(1); 34-39, (2000).

Belardelli et al., Interfron-Alpha in Tumor Immunity and Immunotherapy, Cytokine & Growth Factor Reviews 13: 119-134, (2002).

Attwood, The Babel of Bioinformatics, Science, 290: 471-473, (2000).

Boon,Tumor Antigens Recognized by Cytolytic T Lymphocytes: Present Perspectives for Specific Immunotherapy, Int. J. Cancer 54: 177-1980, (1993).

Spitler, Cancer Vaccines: The Interferon Analogy, Cancer Biotherapy 10: 1-3, (1995).

Ezzell, Cancer "Vaccines": An Idea Whose Time Has Come, J. Hin Research 7: 46-49, (1995).

Taraban et al., Cutting Edge: A Critcal Role for CD70 in CD8 T Cell Priming by DC40-Licensed APCs, The Journal of Immunology Cutting Edge, (2004), pp. 6542-6546.

Di Pucchio et al., Immunization of Stage IV Melanoma Patients With Melan-A/Mart-1 and GP100 Peptides IFN-Alpha Results in the Activation of Specific CD8, T Cells and Monocyte/Dendritic Cell Precursors, Research Article, www.aacrjournals.org., Cancer Res 2006, 66: (9), (May 1, 2006), pp. 4943-4951.

Ahonen et al, Combined T1R and CD40 Triggering Induces Potent CD8+, T Cell Expansion With Variable Dependence on Type 1 IFN, The Journal of Experimental Medicine, vol. 199, No. 6, (Mar. 15, 2004), pp. 775-784.

Santini et al., The Natural Alliance Between Type 1 Interferon and Dendritic Cells and Its Role in Linking Innate and Adaptive Immunity. Journal of Interferon & Cytokine Research 22: 1071-1080 (2002).

* cited by examiner

FGK.45 Ig-light chain

5' - P10 promoter -
<uncut sequence>
    XhoI
CATG[____]TCAGA[ATG]GAGACAGACAGACTCCTGCTATGGGTGCTGCTG
CTCTGGGTGCCAGGCTCCACTGGTGACACTGTACTGACCCAGTCTCCTGCTTT
GGCTGTGTCTCCAGGAGAGAGGGTTACCATCTCCTGTAGGGCCAGTGACAGT
GTCAGTACACTTATGCACTGGTACCAACAGAAACCAGGACAGCAACCCAAAC
TCCTCATCTATCTAGCATCACACCTAGAATCTGGGGTCCCTGCCAGGTTCAGT
GGCAGTGGGTCTGGGACAGACTTCACCCTCACCATTGATCCTGTGGAGGCTG
ATGACACTGCAACCTATTACTGTCAGCAGAGTTGGAATGATCCGTGGACGTT
CGGTGGAGGCACCAAGCTGGAATTGAAACGGGCTGATGCTGCACCAACTGTA
TCTATCTTCCCACCATCCACGGAACAGTTAGCAACTGGAGGTGCCTCAGTCGT
GTGCCTCATGAACAACTTCTATCCCAGAGACATCAGTGTCAAGTGGAAGATT
GATGGCACTGAACGACGAGATGGTGTCCTGGACAGTGTTACTGATCAGGACA
GCAAAGACAGCACGTACAGCATGAGCAGCACCCTCTCGTTGACCAAGGCTGA
CTATGAAAGTCATAACCTCTATACCTGTGAGGTTGTTCATAAGACATCATCCT
CACCCGTCGTCAAGAGCTTCAACAGGAATGAGTGTTAGACCC[____]CATG
                                                                BspEI

FIG. 15A

PGK.45 Ig-heavy chain

```
ggagccagt cctggactct gaggttctcc cactcagtaa tcagtactga
agcactgcac agactcctca ccatggacat caggctcagc ttggttttcc
ttgtccttt cataaaaggt gtccagtgtg aagtgcagct ggtggagtct
ggcggaggct tagtacagcc tggaaggtcc ctgaaactct cctgtgcagc
ctcaggattc actttcagtg actataacat ggcctgggtc cgccaggctc
caaagaaggg tctggagtgg gtcgcaacca tta
                                   tgca acaaacgat ggttattatt aca
                                                                aaaagtaact
ccatggtgac cctgggatgc ctggtcaagg gctatttccc tgagccagtc
accgtgacct ggaactctgg agccctgtcc agcggtgtgc acacttccc
agctgtcctg cagtctggac tctacactct caccagctca gtgactgtac
cctccagcac ctggtccagc caggccgtca cctgcaacgt agcccaccg
gccagcagca ccaaggtgga caagaaaatt gtgccaaggg aatgcaatcc
ttgtggatgt acaggctcag aagtatcatc tgtcttcatc ttccccccaa
agaccaaaga tgtgctcacc atcactctga ctcctaaggt cacgtgtgtt
gtggtagaca ttagccagaa tgatccgag gtccggttca gctggtttat
agatgacgtg gaagtccaca cagctcagac tcatgcccg gagaagcagt
ccaacagcac tttacgctca gtcagtgaac tcccatcgt gcaccgggac
tggctcaatg gcaagacgtt caaatgcaaa gtcaacagtg gagcattccc
tgccccatc gagaaaagca tctccaaacc cgaaggcaca ccacgaggtc
cacaggtata ccatggcg cctcccaagg aagagatgac ccagagtcaa
gtcagtatca cctgcatggt aaaggcttc tatccccag acatttatac
ggagtggaag atgaacggc agccacagga aactacaag aacactccac
ctacgatgga cacagatggg agttacttcc tctacagcaa gctcaatgta
aagaaagaaa catggcagca gggaaacact ttcacgtgtt ctgtgctgca
tgagggcctg cacaaccacc atactgagaa gagtctctcc cactctcctg
gtaaatgatc ccagagtcca gtggccctc ttggctaaa ggatgccaac
acctacctct accactttc tctgtgtaaa taaagcaccc agctctgcct
tgggaccctg caaaaaaaaa aaaaaaaaa aaaaaaa
```

FIG. 15B

SEQUENCE LISTING

```
<160> NUMBER OF SEQ ID NOS: 5

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Ile Ile Asn Phe Glu Lys Leu
  1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Ser Ile Phe Phe Ala Arg Leu
  1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Thr Ser Tyr Lys Ser Glu Phe Val
```

<210> SEQ ID NO 4
<211> LENGTH: 720
<212> TYPE: DNA
<213> ORGANISM: Unknown Organism
<220> FEATURE:
<223> OTHER INFORMATION: Description of Unknown Organism: Unknown Ig-light chain CD40

<400> SEQUENCE: 4

| | | | | | |
|---|---|---|---|---|---|
| catgtcagag | atggagacag | acagactcct | gctatgggtg | ctgctgctct | gggtgccagg | 60 |
| ctccactggt | gacactgtac | tgacccagtc | tcctgctttg | gctgtgtctc | aggagagag | 120 |
| ggttaccatc | tcctgtaggg | ccagtgacag | tgtcagtaca | cttatgcact | ggtaccaaca | 180 |
| gaaaccagga | cagcaaccca | aactcctcat | ctatctagca | tcacacctag | aatctggggt | 240 |
| ccctgccagg | ttcagtggca | gtgggtctgg | gacagacttc | accctcacca | ttgatcctgt | 300 |
| ggaggctgat | gacactgcaa | cctattactg | tcagcagagt | tggaatgatc | cgtggacgtt | 360 |
| cggtggaggc | accaagctgg | aattgaaacg | ggctgatgct | gcaccaactg | tatctatctt | 420 |
| cccaccatcc | acggaacagt | tagcaactgg | aggtgcctca | gtcgtgtgcc | tcatgaacaa | 480 |
| cttctatccc | agagacatca | gtgtcaagtg | gaagattgat | ggcactgaac | gacgagatgg | 540 |
| tgtcctggac | agtgttactg | atcaggacag | caaagacagc | acgtacagca | tgagcagcac | 600 |
| cctctcgttg | accaaggctg | actatgaaag | tcataacctc | tatacctgtg | aggttgttca | 660 |
| taagacatca | tcctcacccg | tcgtcaagag | cttcaacagg | aatgagtgtt | agaccccatg | 720 |

<210> SEQ ID NO 5
<211> LENGTH: 1357
<212> TYPE: DNA
<213> ORGANISM: Unknown Organism
<220> FEATURE:
<223> OTHER INFORMATION: Description of Unknown Organism: Unknown Ig-heavy chain CD40

<400> SEQUENCE: 5

| | | | | | |
|---|---|---|---|---|---|
| ggagcccagt | cctggactct | gaggttctcc | cactcagtaa | tcagtactga | agcactgcac | 60 |
| agactcctca | ccatggacat | caggctcagc | ttggttttcc | ttgtcctttt | cataaaaggt | 120 |
| gtccagtgtg | aagtgcagct | ggtggagtct | ggcggaggct | tagtacagcc | tggaaggtcc | 180 |
| ctgaaactct | cctgtgcagc | ctcaggattc | actttcagtg | actataacat | ggcctgggtc | 240 |
| cgccaggctc | caaagaaggg | tctggagtgg | gtcgcaacca | ttatgcaaca | aaccgatggt | 300 |
| tattattaca | aaagtaact | ccatggtgac | cctgggatgc | ctggtcaagg | gctatttccc | 360 |
| tgagccagtc | accgtgacct | ggaactctgg | agccctgtcc | agcggtgtgc | acaccttccc | 420 |
| agctgtcctg | cagtctggac | tctacactct | caccagctca | gtgactgtac | cctccagcac | 480 |
| ctggtccagc | caggccgtca | cctgcaacgt | agcccacccg | gccagcagca | ccaaggtgga | 540 |
| caagaaaatt | gtgccaaggg | aatgcaatcc | ttgtggatgt | acaggctcag | aagtatcatc | 600 |
| tgtcttcatc | ttccccccaa | agaccaaaga | tgtgctcacc | atcactctga | ctcctaaggt | 660 |
| cacgtgtgtt | gtggtagaca | ttagccagaa | tgatcccgag | gtccggttca | gctggtttat | 720 |
| agatgacgtg | gaagtccaca | cagctcagac | tcatgccccg | gagaagcagt | ccaacagcac | 780 |
| tttacgctca | gtcagtgaac | tccccatcgt | gcaccgggac | tggctcaatg | gcaagacgtt | 840 |
| caaatgcaaa | gtcaacagtg | gagcattccc | tgccccatc | gagaaaagca | tctccaaacc | 900 |
| cgaaggcaca | ccacgaggtc | cacaggtata | caccatggcg | cctcccaagg | aagagatgac | 960 |

```
ccagagtcaa gtcagtatca cctgcatggt aaaaggcttc tatcccccag acatttatac    1020
ggagtggaag atgaacgggc agccacagga aaactacaag aacactccac ctacgatgga    1080
cacagatggg agttacttcc tctacagcaa gctcaatgta aagaaagaaa catggcagca    1140
gggaaacact ttcacgtgtt ctgtgctgca tgagggcctg cacaaccacc atactgagaa    1200
gagtctctcc cactctcctg gtaaatgatc ccagagtcca gtggcccctc ttggcctaaa    1260
ggatgccaac acctacctct accaccttc tctgtgtaaa taaagcaccc agctctgcct    1320
tgggaccctg caaaaaaaaa aaaaaaaaa aaaaaa                               1357
```

IMMUNOSTIMULATORY REGIMEN COMPRISING ADMINISTERING TYPE 1 INTERFERON AND AGONISTIC ANTI-CD40 ANTIBODY

RELATED APPLICATIONS

This application is a Divisional of U.S. application Ser. No. 13/165,154, now U.S. Pat. No. 8,137,672, which is a Divisional of U.S. application Ser. No. 11/743,978 filed on May 3, 2007, now U.S. Pat. No. 7,993,648, which claims priority to U.S. Provisional Applications No. 60/796,867 filed on May 3, 2006, 60/809,821 filed on Jun. 1, 2006 and 60/842,009 filed on Sep. 5, 2006, all of which applications are incorporated by reference in their entirety. Also, the application relates to but does not claim priority to U.S. Provisional Application 60/777,569 filed on Mar. 1, 2006, which application is also incorporated by reference herein.

FIELD OF THE INVENTION

The invention generally relates to synergistic adjuvant combinations which may be used to enhance immunity in subjects in need thereof. More particularly, the invention relates to a specific synergistic adjuvant combination comprising (i) a type 1 interferon and (ii) a CD40 agonist, e.g., an agonistic anti-CD40 antibody or a CD40L polypeptide or CD40L fragment or CD40L containing conjugate, and optionally further including (iii) a target antigen.

Additionally, the invention relates to novel protein or DNA conjugates comprising or encoding said synergistic adjuvant combination such as protein and DNA conjugates which comprise or encode (i) a CD40 agonistic antibody or a soluble CD40L protein or CD40L fragment or CD40L conjugate and (ii) a type 1 interferon and optionally (iii) a desired antigen.

Still further the invention provides novel immune therapies comprising the administration of such synergistic adjuvant combinations or DNA or protein conjugates to enhance antigen specific cellular immunity, e.g., CD8+ immunity. Specifically, the use of compositions comprising these novel adjuvant combinations and/or or polypeptide conjugates and DNA conjugates for treating various chronic diseases including cancer, for example CD40 antigen expressing tumors, and for treating infectious diseases such as HIV infection, autoimmune diseases, allergic and inflammatory diseases, and for potentiating the efficacy of vaccines is also taught.

Also the invention provides novel methods for alleviating the toxicity of CD40 agonists such as CD40L polypeptides and conjugates or agonistic CD40 antibodies by co-administering such CD40 agonist with an amount of a type 1 interferon sufficient to alleviate or prevent toxicity, e.g., liver toxicity that would otherwise result upon administration of the CD40 agonist alone. This facilitates the administration of CD40 agonists at therapeutic dosages which would otherwise be precluded based on toxicity.

BACKGROUND OF THE INVENTION

The body's defense system against microbes as well as the body's defense against other chronic diseases such as those affecting cell proliferation is mediated by early reactions of the innate immune system and by later responses of the adaptive immune system. Innate immunity involves mechanisms that recognize structures which are for example characteristic of the microbial pathogens and that are not present on mammalian cells. Examples of such structures include bacterial liposaccharides, (LPS) viral double stranded DNA, and unmethylated CpG DNA nucleotides. The effector cells of the innate immune response system comprise neutrophils, macrophages, and natural killer cells (NK cells). In addition to innate immunity, vertebrates, including mammals, have evolved immunological defense systems that are stimulated by exposure to infectious agents and that increase in magnitude and effectiveness with each successive exposure to a particular antigen. Due to its capacity to adapt to a specific infection or antigenic insult, this immune defense mechanism has been described as adaptive immunity. There are two types of adaptive immune responses, called humoral immunity, involving antibodies produced by B lymphocytes, and cell-mediated immunity, mediated by T lymphocytes.

Two types of major T lymphocytes have been described, CD8+ cytotoxic lymphocytes (CTLs) and CD4 helper cells (Th cells). CD8+ T cells are effector cells that, via the T cell receptor (TCR), recognize foreign antigens presented by class I MHC molecules on, for instance, virally or bacterially infected cells. Upon recognition of foreign antigens, CD8+ cells undergo an activation, maturation and proliferation process. This differentiation process results in CTL clones which have the capacity of destroying the target cells displaying foreign antigens. T helper cells on the other hand are involved in both humoral and cell-mediated forms of effector immune responses. With respect to the humoral, or antibody immune response, antibodies are produced by B lymphocytes through interactions with Th cells. Specifically, extracellular antigens, such as circulating microbes, are taken up by specialized antigen-presenting cells (APCs), processed, and presented in association with class II major histocompatibility complex (MHC) molecules to CD4+ Th cells. These Th cells in turn activate B lymphocytes, resulting in antibody production. The cell-mediated, or cellular, immune response, in contrast, functions to neutralize microbes which inhabit intracellular locations, such as after successful infection of a target cell. Foreign antigens, such as for example, microbial antigens, are synthesized within infected cells and resented on the surfaces of such cells in association with Class I MHC molecules. Presentation of such epitopes leads to the above-described stimulation of CD8+ CTLs, a process which in turn also stimulated by CD4+ Th cells. Th cells are composed of at least two distinct subpopulations, termed Th1 and Th2 cells. The Th1 and Th2 subtypes represent polarized populations of Th cells which differentiate from common precursors after exposure to antigen.

Each T helper cell subtype secretes cytokines that promote distinct immunological effects that are opposed to one another and that cross-regulate each other's expansion and function. Th1 cells secrete high amounts of cytokines such as interferon (IFN) gamma, tumor necrosis factor-alpha (TNF-alpha), interleukin-2 (IL-2), and IL-12, and low amounts of IL-4. Th1 associated cytokines promote CD8+ cytotoxic T lymphocyte T lymphocyte (CTL) activity and are most frequently associated with cell-mediated immune responses against intracellular pathogens. In contrast, Th2 cells secrete high amounts of cytokines such as IL-4, IL-13, and IL-10, but low IFN-gamma, and promote antibody responses. Th2 responses are particularly relevant for humoral responses, such as protection from anthrax and for the elimination of helminthic infections.

Whether a resulting immune response is Th1 or Th2-driven largely depends on the pathogen involved and on factors in the cellular environment, such as cytokines. Failure to activate a T helper response, or the correct T helper subset, can result not only in the inability to mount a sufficient response to combat a particular pathogen, but also in the generation of poor immunity against reinfection. Many infectious agents are intracellular pathogens in which cell-mediated responses, as exemplified by Th1 immunity, would be expected to play an important role in protection and/or therapy. Moreover, for many of these infections it has been shown that the induction of inappropriate Th2 responses negatively affects disease outcome. Examples include *M. tuberculosis, S. mansoni*, and also counterproductive Th2-like dominated immune responses. Lepromatous leprosy also appears to feature a prevalent, but inappropriate, Th2-like response. HIV infection represents another example. There, it has been suggested that a drop in the ratio of Th1-like cells to other Th cell populations can play a critical role in the progression toward disease symptoms.

As a protective measure against infectious agents, vaccination protocols for protection from some microbes have been developed. Vaccination protocols against infectious pathogens are often hampered by poor vaccine immunogenicity, an inappropriate type of response (antibody versus cell-mediated immunity), a lack of ability to elicit long-term immunological memory, and/or failure to generate immunity against different serotypes of a given pathogen. Current vaccination strategies target the elicitation of antibodies specific for a given serotype and for many common pathogens, for example, viral serotypes or pathogens. Efforts must be made on a recurring basis to monitor which serotypes are prevalent around the world. An example of this is the annual monitoring of emerging influenza A serotypes that are anticipated to be the major infectious strains.

To support vaccination protocols, adjuvants that would support the generation of immune responses against specific infectious diseases further have been developed. For example, aluminum salts have been used as a relatively safe and effective vaccine adjuvants to enhance antibody responses to certain pathogens. One of the disadvantages of such adjuvants is that they are relatively ineffective at stimulating a cell-mediated immune response and produce an immune response that is largely Th2 biased.

It is now widely recognized that the generation of protective immunity depends not only on exposure to antigen, but also the context in which the antigen is encountered. Numerous examples exist in which introduction of a novel antigen into a host in a non-inflammatory context generates immunological tolerance rather than long-term immunity whereas exposure to antigen in the presence of an inflammatory agent (adjuvant) induces immunity. (Mondino et al., Proc. Natl. Acad. Sci., USA 93:2245 (1996); Pulendran et al., J. Exp. Med. 188:2075 (1998); Jenkins et al., Immunity 1:443 (1994); and Kearney et al., Immunity 1:327 (1994)).

A naturally occurring molecule well known to regulate adaptive immunity is CD40. CD40 is a member of the TNF receptor superfamily and is essential for a spectrum of cell-mediated immune responses and required for the development of T cell dependent humoral immunity (Aruffo et al., Cell 72:291 (1993); Farrington et al., Proc Natl Acad. Sci., USA 91:1099 (1994); Renshaw et al., J Exp Med 180:1889 (1994)). In its natural role, CD40-ligand expressed on CD4+ T cells interacts with CD40 expressed on DCs or B cells, promoting increased activation of the APC and, concomitantly, further activation of the T cell (Liu et al Semin Immunol 9:235 (1994); Bishop et al., Cytokine Growth Factor Rev 14:297 (2003)). For DCs, CD40 ligation classically leads to a response similar to stimulation through TLRs such as activation marker upregulation and inflammatory cytokine production (Quezada et al. Annu Rev Immunol 22:307 (2004); O'Sullivan B and Thomas R *Crit. Rev Immunol* 22:83 (2003)) Its importance in CD8 responses was demonstrated by studies showing that stimulation of APCs through CD40 rescued CD4-dependent CD8+ T cell responses in the absence of CD4 cells (Lefrancois et al., J. Immunol. 164:725 (2000); Bennett et al., Nature 393:478 (1998); Ridge et al., Nature 393:474 (1998); Schoenberger et al., Nature 393:474 (1998). This finding sparked much speculation that CD40 agonists alone could potentially rescue failing CD8+ T cell responses in some disease settings.

Other studies, however, have demonstrated that CD40 stimulation alone insufficiently promotes long-term immunity. In some model systems, anti-CD40 treatment alone insufficiently promoted long-term immunity. Particularly, anti-CD40 treatment alone can result in ineffective inflammatory cytokine production, the deletion of antigen-specific T cells (Mauri et al. Nat Med 6:673 (2001); Kedl et al. Proc Natl Acad. Sci., USA 98:10811 (2001)) and termination of B cell responses (Erickson et al., J Clin Invest 109:613 (2002)). Also, soluble trimerized CD40 ligand has been used in the clinic as an agonist for the CD40 pathway and what little has been reported is consistent with the conclusion that stimulation of CD40 alone fails to reconstitute all necessary signals for long term CD8+ T cell immunity (Vonderheide et al., J Clin Oncol 19:3280 (2001)).

Various agonistic antibodies have been reported by different groups. For example, one mAb CD40.4 (5c3) (PharMingen, San Diego Calif.) has been reported to increase the activation between CD40 and CD40L by approximately 30-40%. (Schlossman et al., Leukocyte Typing, 1995, 1:547-556). Also, Seattle Genetics in U.S. Pat. No. 6,843,989 allege to provide methods of treating cancer in humans using an agonistic anti-human CD40 antibody. Their antibody is purported to deliver a stimulatory signal, which enhances the interaction of CD40 and CD40L by at least 45% and enhances CD40L-mediated stimulation and to possess in vivo neoplastic activity. They derive this antibody from S2C6, an agonistic anti-human CD40 antibody previously shown to deliver strong growth-promoting signals to B lymphocytes. (Paulie et al., 1989, J. Immunol. 142:590-595).

Because of the role of CD40 in innate and adaptive immune responses, CD40 agonists including various CD40 agonistic antibodies have been explored for usage as vaccine adjuvants and in therapies wherein enhanced cellular immunity is desired. Recently, it was demonstrated by the inventor and others that immunization with antigen in combination with some TLR agonists and anti-CD40 treatment (combined TLR/CD40 agonist immunization) induces potent CD8+ T cell expansion, eliciting a response 10-20 fold higher than immunization with either agonist alone (Ahonen et al., J Exp Med 199:775 (2004)). This was the first demonstration that potent CD8+ T cell responses can be generated in the absence of infection with a viral or microbial agent. Antigen specific CD8+ T cells elicited by combined TLR/CD40 agonist immunization demonstrate lytic function, gamma interferon production, and enhanced secondary responses to antigenic challenge. Synergistic activity with anti-CD40 resulting in the induction of CD8+ T cell expansion has been shown with agonists of TLR1/6, 2/6, 3, 4, 5, 7 and 9.

To increase the effectiveness of an adaptive immune response, such as in a vaccination protocol or during a microbial infection, it is therefore important to develop novel, more effective, vaccine adjuvants. The present invention satisfies this need and provides other advantages as well.

Also, it is important to develop effective immune adjuvants which are effective at doses which do not elicit adverse side effects such as liver toxicity. Particularly it has been reported by Vanderheide et al., J. Clin. Oncol. 25(7)876-8833(March 2007) that a 0.3 mg/kg is the maximum tolerated dose for an exemplified agonistic antibody and that higher doses may elicit side effects including venous thromboembolism, grade 3 headache, cytokine release resulting in toxic effects such as chills and the like, and transient liver toxicity. Also, it has been reported by Vanderheide et al., J. Clin. Oncol. 19(23):4351-3 (2001) that the maximum tolerated dose for a hCD40L polypeptide described therein was 0.1 mg/kg/day and that when the polypeptide was administered at higher doses of 0.15 mg/kg/day they observed liver toxicity characterized by grade 3 or 4 liver transaminase elevated levels in subjects treated.

SUMMARY OF THE INVENTION

This invention in one embodiment involves the discovery that certain moieties in combination upregulate CD70 on dendritic cells and elicit a synergistic effect on immunity, e.g., they promote Th1 cellular immunity and CD8 T cell immune responses. Particularly, the invention involves the discovery that type 1 interferons and CD40 agonists, such as agonistic CD40 antibodies or CD40L polypeptides or CD40L conjugates, when administered in combination in the same or separate compositions, and further optionally in combination with a desired antigen, elicit a synergistic effect on immunity by inducing CD70 expression on CD8+ dendritic cells and moreover elicit potent expansion of CD8+ T cells and enhanced Th1 immunity.

Based on this discovery, the present invention provides novel adjuvant combinations that can be administered to subjects in need thereof as a means of enhancing immunity. Also, this adjuvant combination can be added to vaccines or administered in conjunction therewith in order to enhance the efficacy thereof.

Related to the said discovery, the invention also provides nucleic acid constructs that encode (i) a type 1 interferon and (ii) a CD40 agonist that optionally may further include (iii) a nucleic acid sequence encoding a desired antigen, which nucleic acid constructs, when administered to a host in need thereof, optionally in conjunction with an antigen, elicit a synergistic effect on immunity. Such CD40 agonists include by way of example CD40 agonistic antibodies and CD40 agonistic antibody fragments, as well as soluble CD40L and CD40L fragments and conjugates and derivatives thereof such as oligomeric CD40L polypeptides, e.g., trimeric CD40L polypeptides and conjugates containing.

Also, the present invention provides polypeptide conjugates comprising (i) at least one type 1 interferon, (ii) at least one CD40 agonist, e.g. a CD40 agonistic antibody or CD40L polypeptide or CD40L fragment or conjugate or derivative thereof such as an oligomeric CD40L or conjugate containing, and optionally (iii) an antigen, wherein these moieties may be directly or indirectly linked, in any order, and elicit a synergistic effect on immunity on administration to a subject in need thereof.

More specifically, this invention provides nucleic acid constructs containing (i) a gene or genes encoding an agonistic anti-human CD40 antibody, or human CD40L polypeptide or fragment, conjugate or derivative thereof, and (ii) a gene encoding a human type 1 interferon, e.g. human alpha or human beta interferon and optionally (iii) a gene encoding an antigen against which an enhanced cellular immune response is desirably elicited.

Also more specifically the invention provides novel polypeptide constructs comprising (i) at least one agonistic anti-human CD40 antibody or a human CD40L polypeptide or fragment thereof that agonizes human CD40/CD40L, a human alpha or beta interferon, and optionally at least one antigen against which an enhanced cellular immune response is desirably elicited.

Still further, the invention provides adjuvant polypeptide compositions comprising synergistically effective amount of (i) a type 1 interferon, preferably alpha or beta interferon, (ii) a CD40 agonist, preferably an agonistic CD40 antibody or a monomeric or oligomeric soluble CD40 L polypeptide or fragment or conjugate thereof, and optionally (iii) one or more antigens.

Also, the invention relates to the discovery that the toxicity of CD40 agonists can potentially be alleviated if the CD40 agonist is administered in conjunction with a type 1 interferon or a TLR agonist. Thereby, the invention provides for more effective CD40 agonist therapies as the CD40 agonist can be administered at higher dosages than heretofore described. For example the MTD (maximum tolerated dosage) of CD40L polypeptide if co-administered with a type 1 interferon or a TLR agonist may exceed 0.1 mg/kg/day by at least 1.5 fold, more preferably by at least 2-5 fold, or even 10-fold or more thereby permitting the CD40L polypeptide to be administered at MTD amounts ranging from at least about 0.15 mg/kg/day to 1.0 mg/kg/day or higher. This will result in more effective CD40L therapies such as in the treatment of CD40 associated malignancies and other treatments disclosed herein. In addition the present invention will reduce toxicity of CD40 agonist antibody therapies and facilitate the administration of CD40 agonist antibody dosages higher than heretofore suggested. Particularly, as noted above it has been reported that the MTD for an agonistic CD40L antibody reported by Vonderheide et al., J. Clin. Immunol. 25(7):876-883 (2007) was 0.3 mg/kg and that dosages in excess resulted in transient liver toxicity, venous thromboembolism, grade 3 headaches and cytokine release and associated toxicity and adverse side effects such a fever and chills. Co-administration of the CD40 agonist antibody in association with type 1 interferon or a TLR agonist potentially allows for the MTD antibody amount to be substantially increased, e.g. by 1.5-15 or even 5-10 fold without adverse effects. Thereby the MTD amount for the CD40 agonistic antibody may be increased to about 0.45 mg/kg to about 3.0 mg/kg or even higher. Thus the invention includes the co-administration of a CD40 agonist with an amount of type 1 interferon or TLR agonist sufficient to reduce toxic effects such as liver toxicity that would otherwise potentially result at the particular CD40 agonist dosage amount.

In addition the invention provides novel therapies comprising administration of any of the foregoing protein or DNA conjugates or synergistic adjuvant protein containing compositions. These therapies include the use thereof as immune agonists (adjuvants) such as to synergistically enhance the efficacy of vaccines and for treating conditions wherein enhanced immunity is desired such as cancer, infectious conditions, autoimmune conditions, allergy, inflammatory conditions and gene therapy.

As noted above and shown infra it has been surprisingly discovered that the afore-described novel adjuvant combination or protein or DNA conjugates encoding elicits a synergistic effect on immunity relative to the administration of the CD40 agonist or the type 1 interferon alone and/or potentially reduces or prevents adverse side effects such as liver toxicity. Such reduced toxicity can e.g., be determined based on the effect of the immunostimulatory combination on liver transaminase levels. This synergism is apparently obtained because the adjuvant combinations of the invention surprisingly induce (upregulate) CD70 expression on CD8+ dendritic cells in vivo, and thereby induce the potent expansion of CD8+ T cells in vivo.

At least based on these surprising synergistic effects on dendritic cells, and on CD8+ T cell immunity and Th1 immunity, compositions containing these adjuvant combinations, nucleic acid constructs, or polypeptide conjugates may be administered to a host in need of thereof as a means of:

(i) generating enhanced (exponentially better) primary and memory CD8+ T cell responses relative to immunization with either agonist alone;
(ii) inducing the exponential expansion of antigen-specific CD8+ T cells, and/or
(iii) generating protective immunity.

Accordingly, these adjuvants combinations which may comprise protein compositions, or nucleic acid constructs encoding or polypeptide conjugates containing may be used in treating any disease or condition wherein the above-identified enhanced cellular immune responses are therapeutically desirable, especially infectious diseases, proliferative disorders such as cancer, allergy, autoimmune disorders, inflammatory disorders, and other chronic diseases wherein enhanced cellular immunity is a desired therapeutic outcome. Preferred applications of the invention include especially the treatment of infectious disorders such as HIV infection and cancer.

DETAILED DESCRIPTION OF THE FIGURES

FIG. 1 shows CD8+ T cell expansion following combined TLR/CD40 agonist immunized is variably dependent on IFN α/β. WT (top row) and IFNαβRKO (bottom row) were immunized with ovalbumin peptide, anti-CD40 and the indicated TLR agonists. 7 days late, the ovalbumin specific T cell responses were measured in the spleen by tetramer staining and FACS analysis. Numbers in the upper right quadrant indicate the percentage of tetramer staining cells out of the total CD8+ T cells.

FIG. 2 shows CD4 depletion of IFNαβRKO hosts restores the CD8+ T cell response after immunization with the IFNαβ-dependent TLR agonist in combination with anti-CD40. WT and IFNαβRKO mice, CD40-depleted or non-depleted as indicated were immunized with HSV-1 peptide, anti-CD40, and polyIC as described above. 7 days later, the HSV-1 specific response was determined by tetramer (A) and polyIC IFNgamma (B) staining PBLs).

Figure 3:
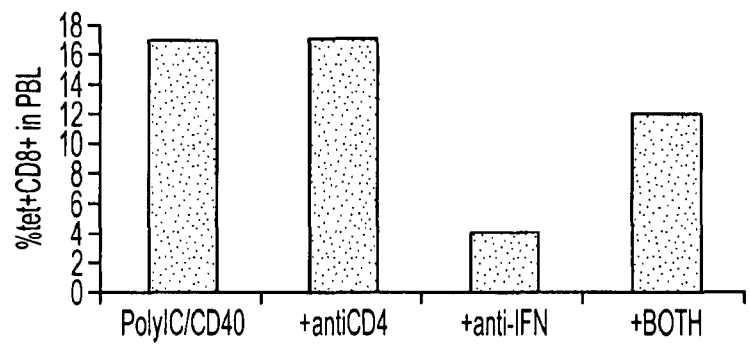

FIG. 3 shows anti-IFN blocks polyIC/CD40 mediated CD8 response which is recovered by CD4-depletion. Mice were immunized against ovalbumin (combined polyIC/alphaCD40) with and without anti-IFN and/or CD4 depletion. Day 7 PBLs were analyzed by tetramer staining as described above, for the antigen-specific T cells.

Figure 4:
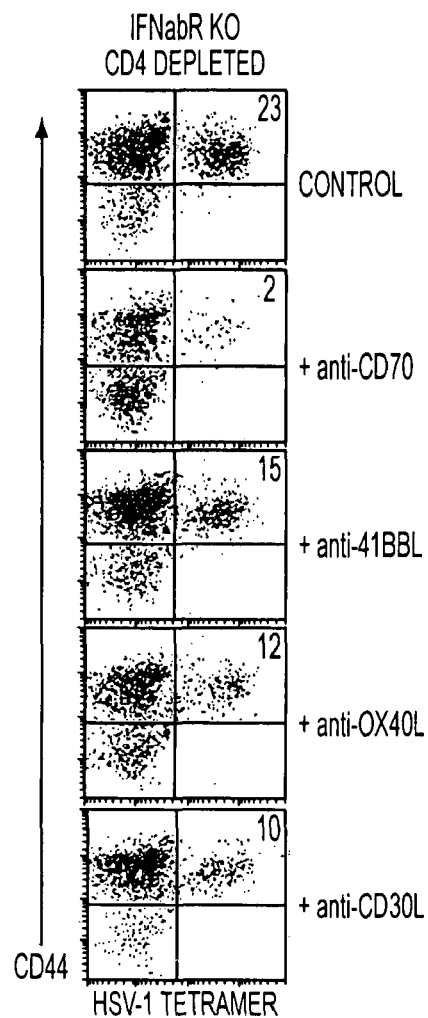

FIG. 4 shows the CD8+ T cell response in CD4-depleted, IFN αβRKO hosts following combined TLR/CD40 immunization is largely dependent on CD70. IFNαβRKO mice were depleted of CD4 cells and immunized with HSV-1 peptide, polyIC and anti-CD40 as described above. Mice were injected with anti-TNF ligand antibodies as in FIG. 6. Day 7 PBLs were analyzed by tetramer staining.

Figure 5A:
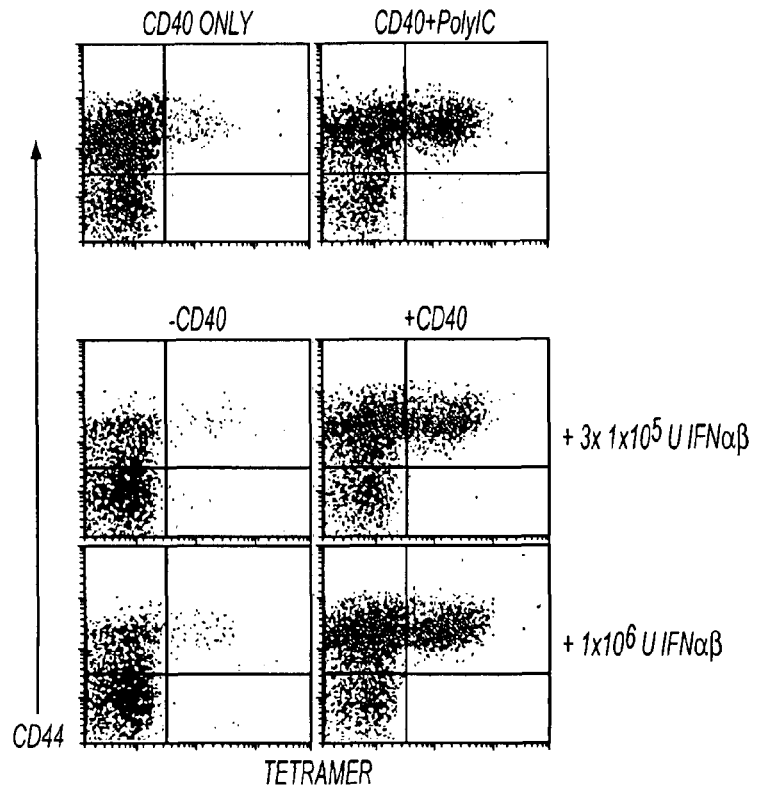
Figure 5B:
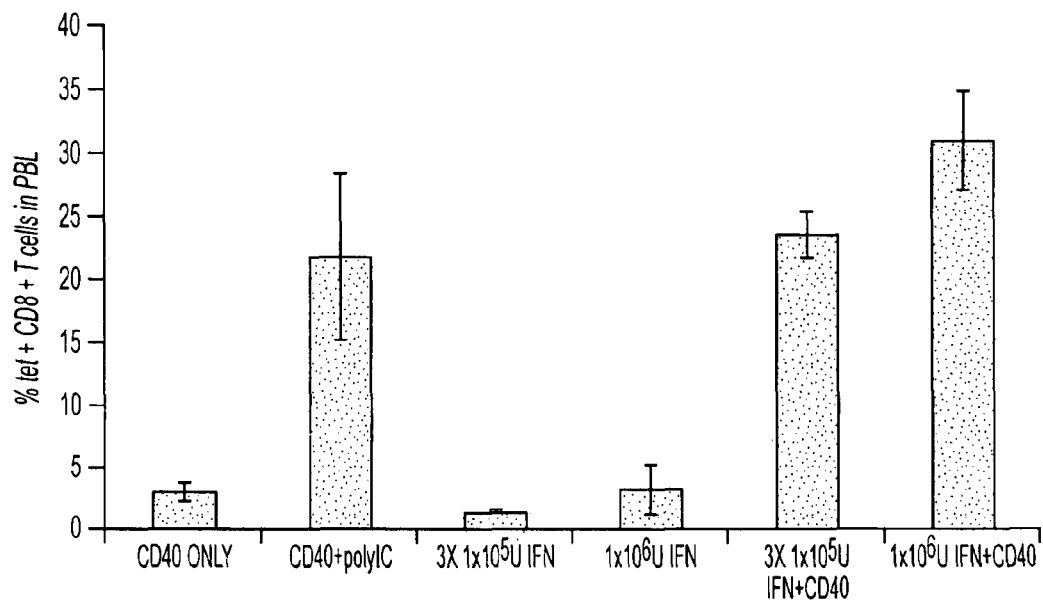

FIG. 5 shows IFN and CD40 synergize to elicit exponential CD8+ T cell expansion. Mice were challenged as described above. 7 days after initial antigen challenge, PBLs were analyzed by tetramer staining.

Figure 6:
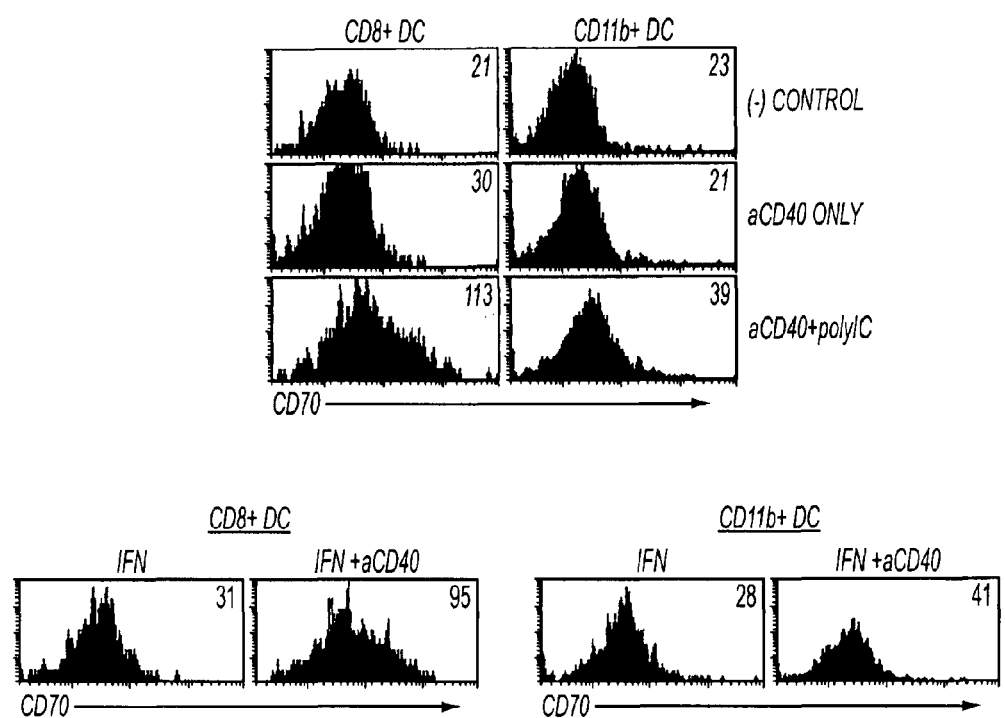

FIG. 6 contains the results of an experiment relating to combined administration of a type 1 interferon and an agonistic antibody showing that this combination induces CD70 expression on CD8+ dendritic cells in vivo whereas administration of either alone does not. Mice were injected with anti-CD40 antibody alone, polyIC as a positive control, recombinant type 1 interferon ($1 \times 10^7$ U) or anti-CD40+IFN. 18 hours later spleen DCs were isolated and analyzed for their expression of CD70. The numbers in the upper right quadrant indicate the mean fluorescence intensity of CD70 staining. The data reveal that, similar to CD40/polyIC injection, CD40/IFN similarly increase the expression of CD70 on CD8+ DCs.

Figure 7:
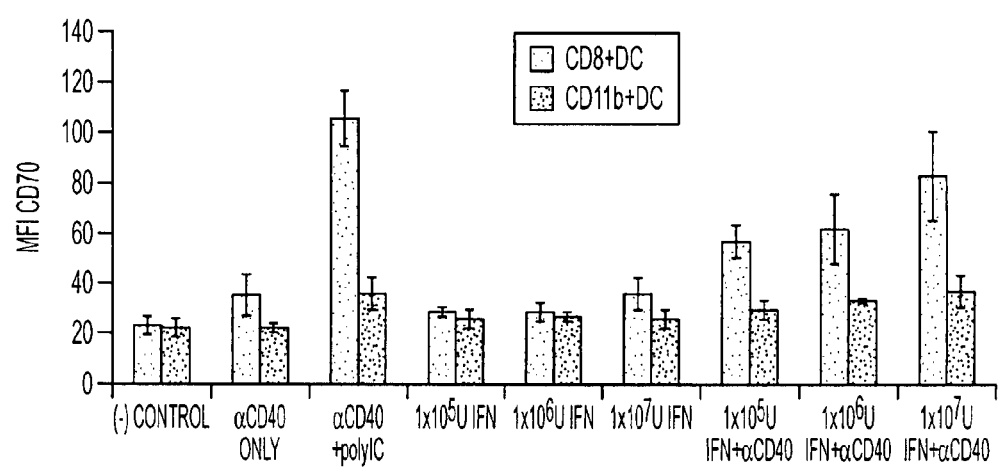

FIG. 7 contains an experiment showing the effect of combined type 1 interferon administration and an agonistic CD40 antibody on CD70 expression on CD8+ DCs in vivo. The results show that only the immunostimulatory combinations and not CD40 agonist or IFN alone induce CD70 expression on DCs.

Figure 8:
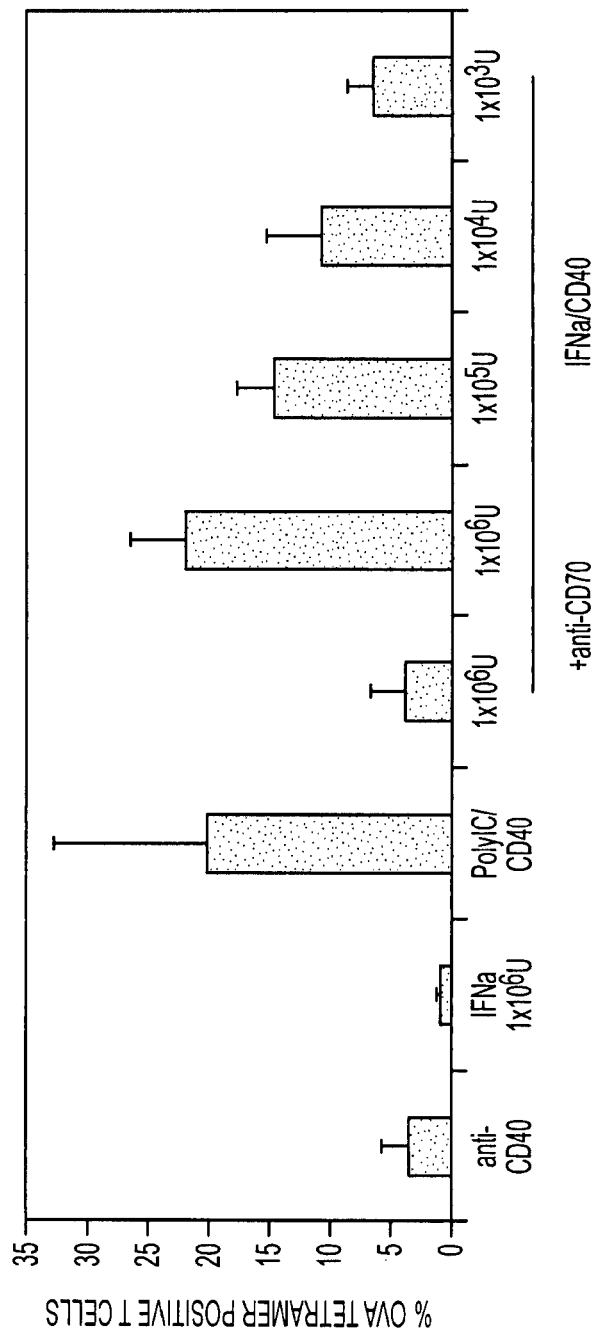

FIG. 8 contains an experiment that analyzed the percentage of antigen-specific (ovalbumin T cells) in mice administered ant-CD40, IFNalpha, polyIC/CD40, IFNalpha and anti-CD70 or IFNalpha/CD40 at various decreasing IFN doses.

Figure 9:
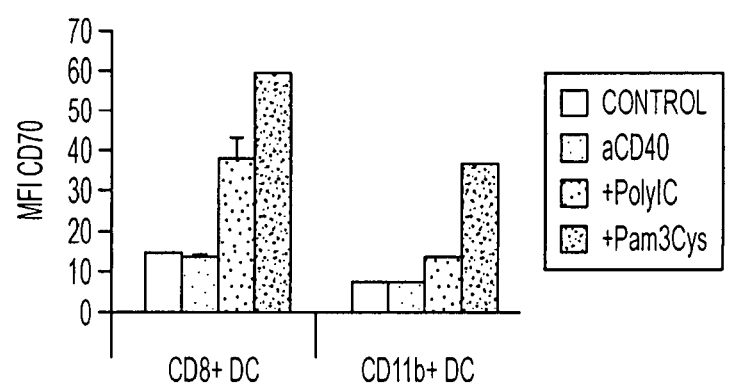

FIG. 9 similarly to the experiment in FIG. 7 shows combined TLR/CD40 agonist challenge induces CD70 expression only on DCs expressing the targeted TLR in IFN αβRKO mice. IFN αβRKO mice were injected with anti-CD40 alone (aCD40) or in combination with polyIC (+ polyIC) or Pam3Cys (+Pam3Cys). Pam3Cys is a TLR2 agonist and PolyIC is a TLR3 agonist. 24 hours later the spleen DCs were isolated and stained for CD70 expression as described above. CD8+ DCs express TLR2 and 3 while CD11b+DCs express TLR2 but not TLR3. The data suggest that in the absence of IFNαβ signaling only DCs stimulated directly through both TLR and CD40 are able to increase CD70 expression.

Figure 10A:
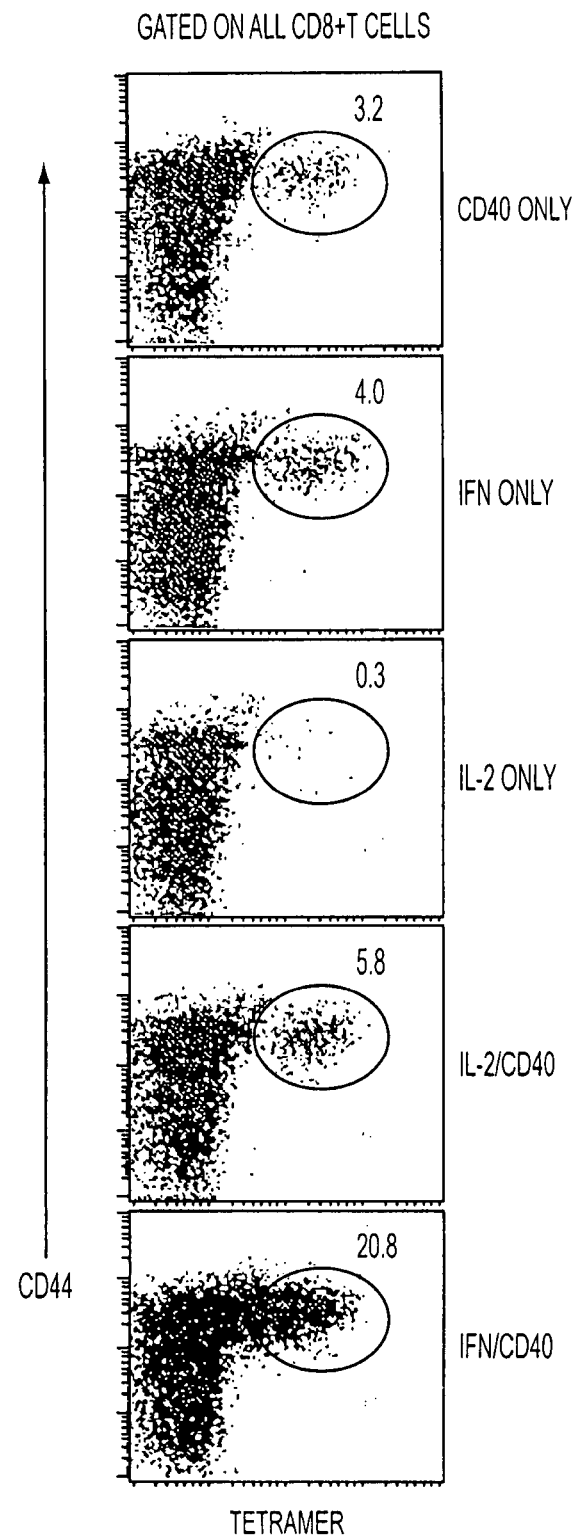
Figure 10B:
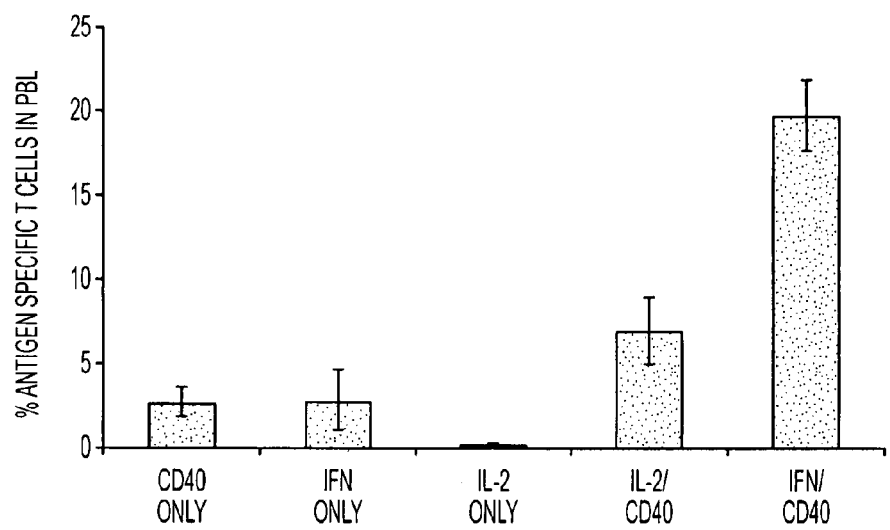

FIG. 10 contains an experiment comparing the effect of IL-2/CD40 agonist combination and IFNalpha/CD40 agonist combination on the percentage of antigen-specific (ovalbumin) T cells from PBLs. The results contained therein show that the IL-2/CD40 agonist combination does not elicit a comparable synergistic effect on CD8+ T cell immunity as the IFNalpha/CD40 agonist combination.

Figure 11:
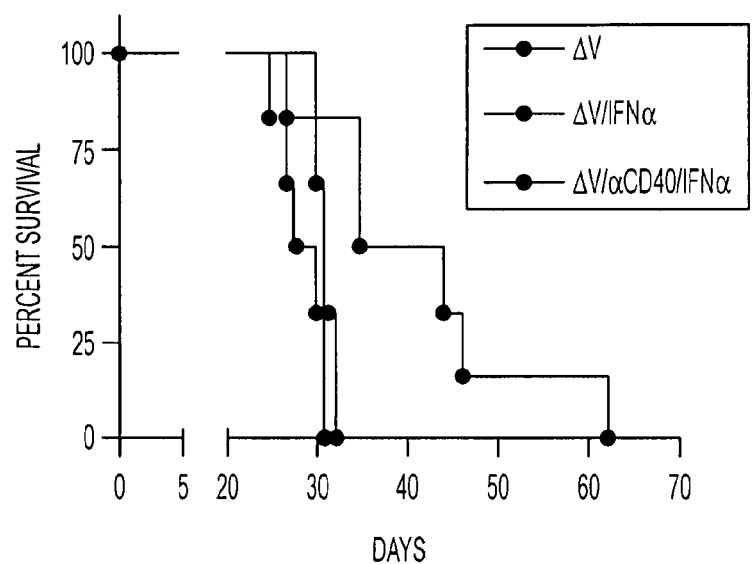

FIG. 11 contains an experiment in C57BI/6 mice with injected melanoma cells showing that the IFNalpha/CD40 agonist combination increased survival time in this metastatic melanoma animal model.

Figure 12A:
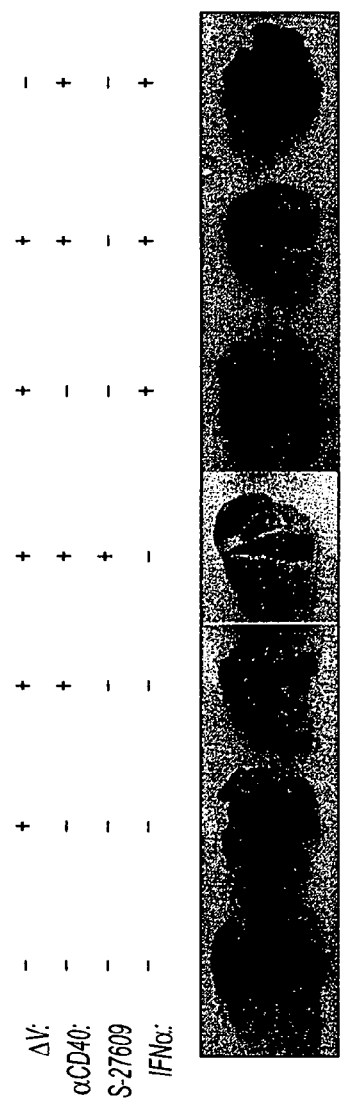
Figure 12B:
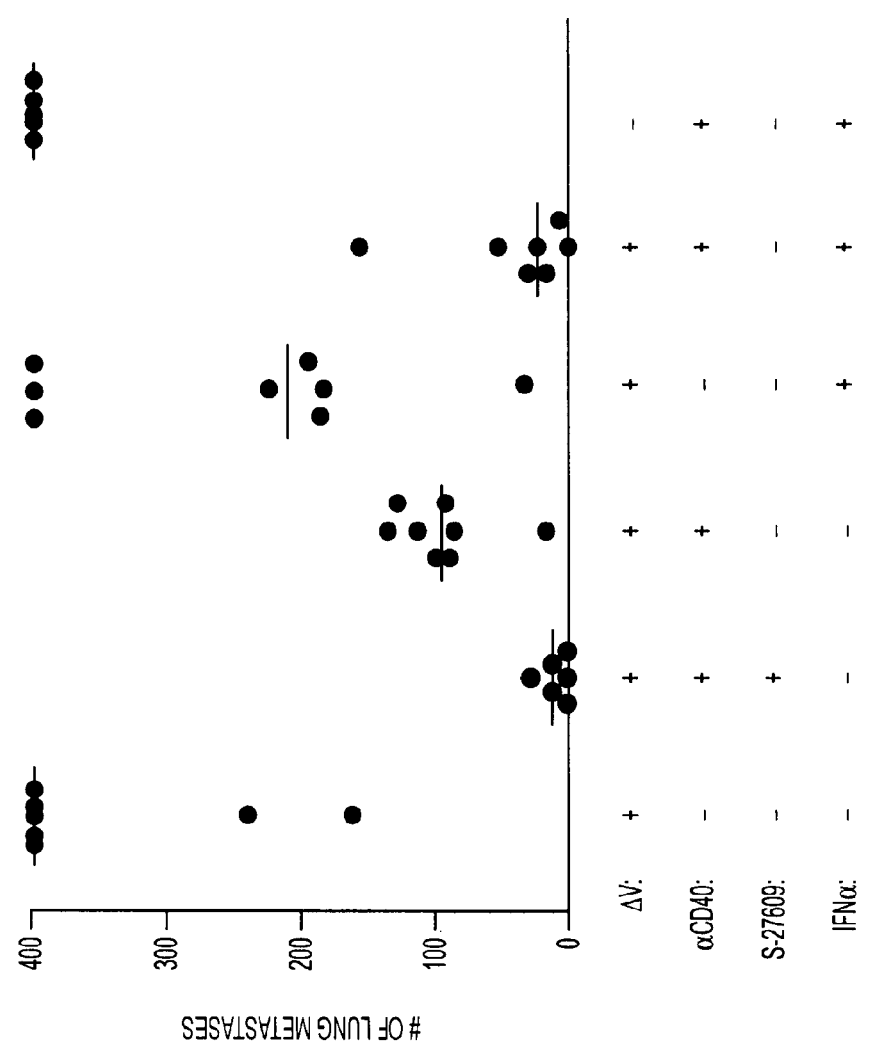
Figure 13A:
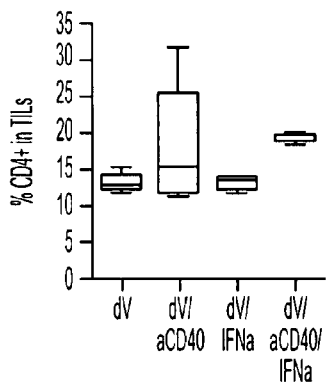
Figure 13D:
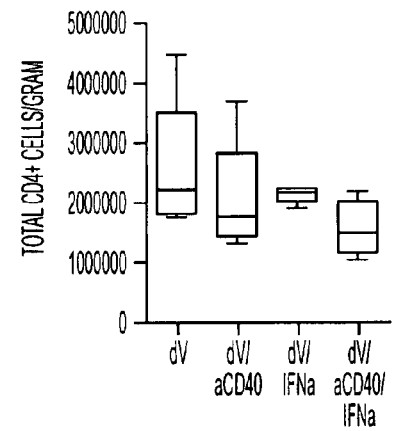
Figure 13B:
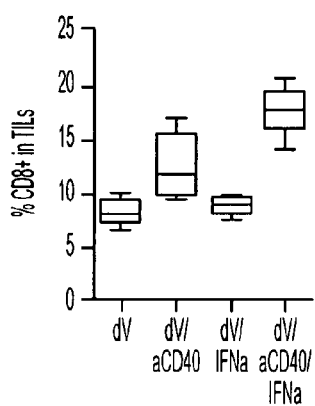
Figure 13E:
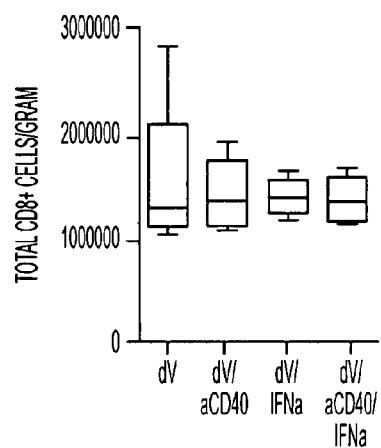
Figure 13C:
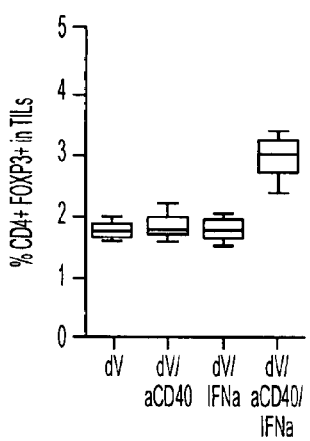
Figure 13F:
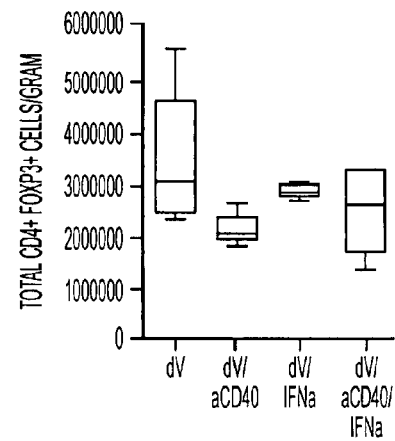

FIG. 12 contains an experiment showing the subject combination adjuvant therapy with CD40 agonist and IFN alpha in a C57BI/6 animal model for metastatic lung cancer protects the mice from metastatic lung cancer as shown by a reduced number of metastatic nodules in animals treated with the adjuvant combination.

FIG. 13 contains an experiment wherein TIL analysis was effected in C57BI/6 mice inoculated with B16.F10 melanoma cells treated with the subject adjuvant combination and appropriate controls. The mice administered the subject adjuvant combination revealed increased numbers of TILs as shown by the data in the Figure.

Figure 14A:
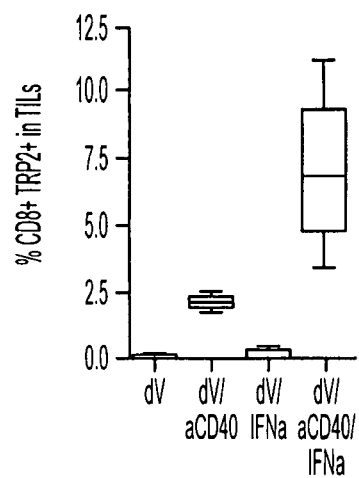
Figure 14B:
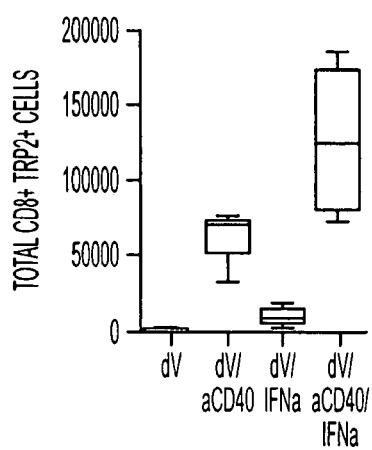

FIG. 14 contains an experiment that shows that the subject CD40 agonist/IFN combination therapy generates antigen-specific effector T cells that infiltrate the lungs of tumor bearing mice (C57BI/6 mice inoculated with B16.F10 melanoma cells)

FIGS. 15A and 15B contain light and heavy chain sequences for the exemplary CD40 agonistic antibody (FGK.45) used in the examples.

Figure 16A:
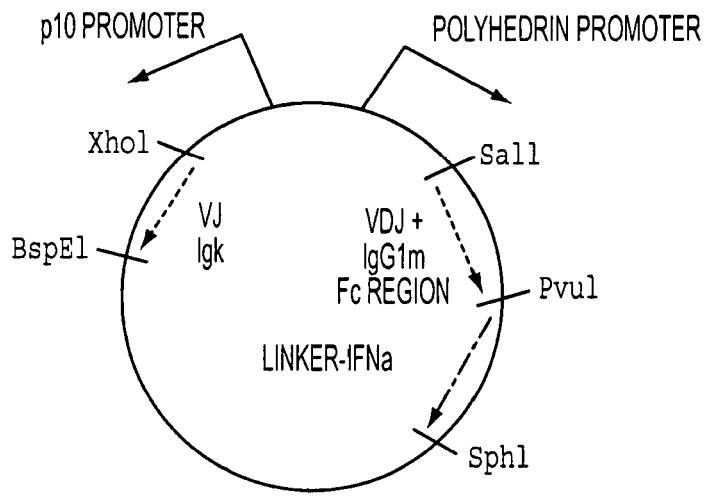
Figure 16B:
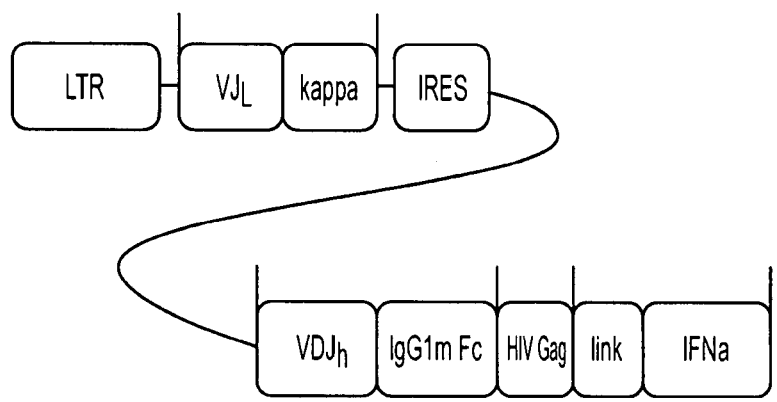

FIG. 16 contains a schematic showing construction of a DNA construct for expression of a CD40 agonistic antibody-antigen-type 1 IFN conjugate in a baculovirus expression system according to the invention. This construct will result in the expression of an anti-CD40 antibody linked to an antigen of choice (e.g. HIV gag) and to a type 1 interferon (alpha interferon).

Figure 17A:
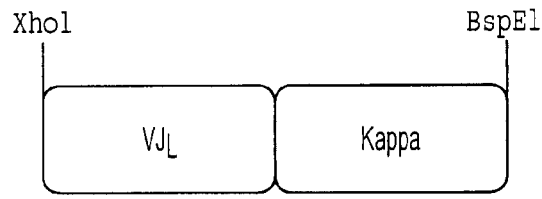
Figure 17B:
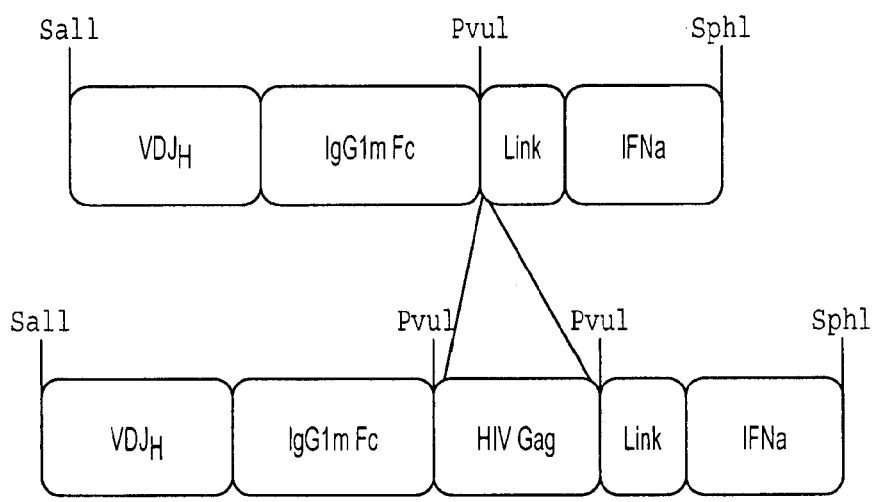

FIG. 17 contains a construct for producing CD40 ab-antigen-type 1 IFN conjugate according to the invention in a baculovirus expression system and a construct for producing a vector for use in DNA immunization.

DETAILED DESCRIPTION OF THE INVENTION

As noted above, the invention generally relates to synergistic adjuvant combinations and use thereof. Prior to discussing the invention in more detail, the following definitions are provided. Otherwise all terms should be construed as they would be a person of skill in the art.

In the present invention, the term "agonist" includes any entity that directly binds and activates a receptor or which indirectly activates a receptor by forming a complex with another entity that binds the receptor or by causing the modification of another compound that thereupon directly binds and activates the receptor.

The term "CD40 agonist" in particular includes any entity which agonizes CD40/CD40L and/or which increases one or more CD40 or CD40L associated activities. This includes by way of example CD40 agonistic antibodies, fragments thereof, soluble CD40L and fragments and derivatives thereof such as oligomeric (e.g., bivalent, trimeric CD40L), and fusion proteins containing and variants thereof produced by recombinant or protein synthesis. In addition such CD40 agonists include small molecules, and CD40 aptamers which comprise RNA or DNA molecules that can be substituted for antibodies. Techniques for the production and use thereof as antigen binding moieties may be found e.g., in U.S. Pat. Nos. 5,475,046; 5,720,163; 5,589,332; and 5,741,679. These patents are incorporated by reference in their entirety herein.

in the present invention the term "CD40L" or "CD154" as it alternatively known in the art includes all mammalian CD40L's, e.g., human, rat, non-human primate, murine as well as fragments, variants, oligomers, and conjugates thereof that bind to at least the corresponding mammalian CD40 polypeptide, e.g., human CD40. In the present invention the administered CD40L may comprise a CD40L polypeptide or a DNA encoding said CD40L polypeptide. Such CD40L polypeptides and DNAs include in particular native CD40L sequences and fragments, variants, and oligomers thereof as disclosed in Immunex U.S. Pat. No. 6,410, 711; U.S. Pat. No. 6,391,637; U.S. Pat. No. 5,981,724; U.S. Pat. No. 5,961,974 and US published application No. 20040006006 all of which patents and application and the CD40L sequences disclosed therein are incorporated by reference in their entirety herein.

In the present invention the term 4-1BB agonist includes any entity that agonizes the 4-1BB receptor such as agonistic 4-1BB antibodies and 4-1mM polypeptides and conjugates thereof. Such agonists potentially can be co-administered with a type 1 interferon or TLR agonist to elicit a synergistic effects on immunity.

In the present invention the term "type 1 interferon" encompasses any type 1 interferon which elicits an enhanced CD8+ immune response when administered proximate to or in combination with a CD40 agonist. This includes alpha interferons, beta interferons and other types of interferons classified as type 1 interferons. Particularly, this includes epsilon interferon, zeta interferon, and tau interferons such as tau 1 2, 3, 4, 5, 6, 7, 8, 9, and 10; Also, this includes variants thereof such as fragments, consensus interferons which mimic the structure of different type 1 interferon molecules such as alpha interferons, PEGylated versions thereof, type 1 interferons with altered glycosylation because of recombinant expression or mutagenesis, and the like. Those skilled in the art are well aware of different type 1 interferons including those that are commercially available and in use as therapeutics. Preferably the type 1 interferon will comprise a human type 1 interferon and most preferably a human alpha interferon.

The term "synergistic adjuvant" or "synergistic combination" in the context of this invention includes the combination of two immune modulators such as a receptor agonist, cytokine, adjuvant polypeptide, that in combination elicit a synergistic effect on immunity relative to either administered alone. Particularly, this application discloses synergistic combinations that comprise at least one type 1 interferon and a CD40 agonist or a TLR agonist and a CD40 agonist or a TLR agonist or type 1 interferon and a 4-1 BB agonist. These synergistic combinations upon administration together or proximate to one another elicit a greater effect on immunity, e.g., relative to when the CD40 agonist or type 1 interferon is administered in the absence of the other moiety. For example, the greater effect may be evidenced by the upregulation of CD70 on dendritic cells in vivo that does not occur when either immune modulator or agonist is administered alone.

"Co-administration" in the present invention refers to the administration of different entities such as a type 1 interferon and a CD40 agonist or a protein conjugate or DNA conjugate or conjugates encoding for same under conditions such that the entities, e.g., CD40 agonist and the type 1 interferon elicit a synergistic effect on immunity and e.g., result in the upregulation of CD70 on dendritic cells and/or reduce adverse side effects such as liver toxicity. The moieties may be administered in the same or different compositions which if separate are administered proximate to one another, generally within 24 hours of each other and more typically within about 1-8 hours of one another, and even more typically within 1-4 hours of each other or close to simultaneous administration. The relative amounts are dosages that achieve the desired synergism. In addition the agonists if administered in the form of DNA conjugates may be comprised on the same or different vector, such as a plasmid or recombinant viral vector such as an adenoviral or vaccinia vector.

"Vaccine" refers to a composition which on administration alone or in conjunction with the adjuvant combination of the invention results in an antigen-specific effect on immunity. This includes prophylactic vaccines which confer protection and therapeutic vaccines.

the term "antibody" refers to an intact antibody or a binding fragment thereof that competes with the intact antibody for specific binding. Binding fragments are produced by recombinant DNA techniques, or by enzymatic or chemical cleavage of intact antibodies. Binding fragments include Fab, Fab', F(ab)2, Fv and single chain antibodies. This includes in particular chimeric, human, humanized, bispecific, and non-human antibodies. Additionally, such antibodies and fragments include variants thereof which are altered to affect one or more properties such as cleavage, glycosylation, effector function, and the like.

As noted above, there is a significant need for the development and implementation of new vaccine adjuvants and/or adjuvant formulations that are able to generate potent antigen-specific T cell immunity and which are not subject to undesired side effects such as liver toxicity.

The present invention satisfies this need by providing novel adjuvants that may be administered alone or in conjunction with existing vaccines in order to enhance their efficacy. These adjuvants will typically include at least one type 1 interferon, preferably alpha or beta human interferon, at least one CD40 agonist (anti-CD40 antibody or fragment thereof) or a soluble CD40L polypeptide.

The present invention provides methods of eliciting enhanced cellular immune responses in subjects in need thereof by administering the combination of at least one CD40 agonist, preferably a CD40 agonistic antibody or soluble CD40L, a type 1 interferon, such as human alpha or beta interferon and optionally a target antigen, e.g., a tumor antigen, autoantigen, allergen or a viral antigen. These moieties elicit a synergistic effect on cellular immunity by eliciting CD70 expression on CD8+ dendritic cells. Specifically, this combination induces the following: (i) exponential increase in generation of primary and memory CD8+ T cell response than either agonist alone (ii) exponential expansion of CD8+ T cells and (iii) should elicit protective immunity. As shown infra the induction of CD70 expression on CD8+ dendritic cells does not occur when either the CD40 agonistic antibody or the type 1 interferon are administered alone. Therefore, the CD40 agonist/IFN combination surprisingly synergizes inducing CD70 expression on CD8+ DCs and potent expansion of CD8+ T cells in vivo.

Related to this discovery the present invention further provides DNA constructs encoding a novel synergistic agonistic polypeptide conjugate that promotes cellular immunity comprising (i) a DNA encoding a CD40 agonist preferably a CD40 agonistic antibody or fragment thereof or a soluble CD40L or fragment or derivative and (ii) a DNA encoding a type 1 interferon, e.g., alpha or beta interferon and which construct preferably further includes (iii) a DNA encoding a desired antigen.

The present invention further provides synergistic protein conjugates that elicit a synergistic effect on cellular immunity comprising a CD40 agonist, preferably a agonistic CD40 antibody or fragment or a fragment of CD40L, a type 1 interferon, and optionally a desired target antigen.

The invention further provides compositions containing these DNA constructs which when administered to a host, preferably a human, may be used to generate enhanced antigen specific cellular immune responses.

The present invention further provides expression vectors and host cells containing a DNA construct encoding said novel synergistic agonistic polypeptide combination comprising (i) a DNA or DNAs encoding a specific CD40 agonist, preferably a agonistic CD40 antibody or antibody fragment or a fragment of CD40L, (ii) a DNA or DNAs encoding a type 1 interferon, preferably alpha or beta interferon and (iii) preferably a DNA that encodes an antigen against which enhanced antigen specific cellular immune response are desirably elicited, e.g. a viral or tumor antigen.

Also, the invention provides methods of using said vectors and host cells to produce a composition containing said novel synergistic IFN/CD40 agonist/antigen polypeptide conjugate, preferably an agonistic CD40 ab/antigen/type 1 interferon polypeptide conjugate.

Further the invention provides methods of administering said DNA constructs or compositions and vehicles containing to a host in which an antigen specific cellular immune response is desirably elicited, for example a person with a chronic disease such as cancer or an infectious or allergic disorder under conditions which preferably reduce or eliminate undesired side effects such as liver toxicity.

Still further the invention provides compositions comprising said novel synergistic IFN/CD40 agonist antigen polypeptide conjugates which are suitable for administration to a host in order to elicit an enhanced antigen-specific cellular immune response.

Also, the present invention provides compositions suitable for therapeutic use comprising the combination of at least one type 1 interferon, at least one CD40 agonist, and optionally a target antigen which elicit a synergistic effect on cellular immunity when administered to a host in need of such administration.

Also, the invention provides novel methods of immunotherapy comprising the administration of said novel synergistic agonist-antigen polypeptide conjugate or a DNA encoding said polypeptide conjugate or a composition or compositions containing at least one type 1 interferon, at least one CD40 agonist and optionally at least one target antigen to a host in need of such treatment in order to elicit an enhanced (antigen specific) cellular immune response. In preferred embodiments these compositions and conjugates will be administered to a subject with or at risk of developing a cancer, an infection, particularly a chronic infectious disease e.g., involving a virus, bacteria or parasite; or an autoimmune, inflammatory or allergic condition. For example the invention may be used to elicit antigen specific cellular immune responses against HIV. HIV is a well recognized example of a disease wherein protective immunity almost certainly will require the generation of potent and long-lived cellular immune responses against the virus.

Also, the invention provides methods of enhancing the efficacy of vaccines, particularly vaccines intended to induce a protective cellular immune response by combining or co-administering the subject synergistic adjuvant combination which upregulates CD70 on dendritic cells. In the preferred embodiment such adjuvant will comprise the specific adjuvants disclosed herein and optionally may further comprise another adjuvant such as a TLR, e.g., a TLR1, TLR2, TLR3, TLR4, TLR5, TLR6, TLR7, TLR8, TLR9, TLR10 or TLR11. Ideally, this additional adjuvant will further induce CD70 expression by dendritic cells and result in further enhanced immune responses in a subject in need thereof.

The present invention is an extension of the inventors' prior demonstration that the immunization with antigen in the presence of agonists for both a toll-like receptor (TLR) and CD40 (combined TLR/CD40 agonist immunization) elicits a vigorous expansion of antigen specific CD8+ T cells. The response elicited from this form of vaccination is exponentially greater than the response elicited by either agonist alone, and is far superior to vaccination by conventional methods. Combined TLR/CD40 agonist immunization has been observed to produce potent primary and secondary CD8+ T cell responses, achieving 50-70% antigen specific T cells in the circulation after only 2 immunizations. However, unlike the inventors' prior invention, the present synergistic combination comprises the combination of a type 1 interferon and a CD40 agonist or a 4-1BB agonist. It has been surprisingly found that both TLR/CD40 agonistic antibody combinations and type 1 interferon/CD40 agonistic antibody combinations induce CD70 expression on CD8+ DCs and thereby elicit potent expansion of CD8+ T cells in vivo. Thus, the CD40 pathway is seemingly integrated with both the TLR and the type 1 IFN signaling pathways providing for the induction of synergistically enhanced DC activation and thereby potent induction of antigen specific cellular immunity.

To elicit a synergistic effect on cellular immunity, the CD40 agonist, the type 1 interferon and an antigen if present are preferably administered as discrete polypeptide moieties which may be jointly or separately administered, in either order, substantially proximate or simultaneous to one another under conditions that result in the desired synergistic effect on immunity. Whether synergism is obtained may be detected by various means, e.g., based on the upregulation of CD70 expression on dendritic cells under the administration conditions. Alternatively, these moieties may be administered as a single polypeptide fusion or conjugates containing these two or three discrete entities or administered in the form of a DNA conjugate or conjugates encoding said two or three discrete entities. The latter two embodiments of the invention are advantageous in the context of a polypeptide or DNA based vaccine since potentially only one active agent will need to be formulated and administered to a subject in need of treatment, for example an individual with HIV infection or cancer.

The present invention satisfies this need by providing novel adjuvants that may be administered alone or in conjunction with existing vaccines in order to enhance their efficacy. These adjuvants will typically include at least one type 1 interferon, preferably alpha or beta human interferon, at least one CD40 agonist (anti-CD40 antibody or fragment thereof or soluble CD40L polypeptide) and preferably at least one antigen against which enhanced antigen-specific cellular immunity is desirably elicited such as a tumor antigen or viral antigen. In a preferred embodiment of the invention these polypeptide moieties will be contained in a single polypeptide conjugate or will be encoded by a nucleic acid construct which upon expression in vitro in a host cell or in vivo upon administration to a host results in the expression of said agonist and antigen polypeptides or the expression of a conjugate containing these polypeptides.

The administered amounts of the type 1 interferon and the CD40 agonist, e.g., an agonistic CD40 antibody will comprise amounts that in combination or co-administration yield a synergistic effect by inducing CD70 expression on dendritic cells and enhanced numbers of antigen specific CD8+ T cells. Ideally, the dosage will not result in adverse side effects such as liver toxicity which can be detected e.g., based on liver transaminase levels. With respect to the type 1 interferon, the amount may vary from about $1 \times 10^3$ units of activity (U) to about $1 \times 10^{10}$ U, more typically from about $10^4$ U to about $10^8$ U. The amount of the agonistic antibody or CD40L polypeptide may vary from about 0.00001 grams to about 5 grams, more typically from about 0.001 grams to about 1 gram. As noted above, a preferred MTD will exceed 0.3 mg/kg and may range from about 0.45 mg/kg to about 3 mg/kg. If the therapeutic method involves the administration of an antigen this may be administered at amounts ranging from about 0.0001 grams to about 50 grams, more typically from about 0.1 grams to about 10 grams. As noted, these moieties may be administered in the same or different formulations. If administered separately the moieties may be administered in any order, typically within several hours of each other, more typically substantially proximate in time.

As noted, the CD40 agonist includes any moiety that agonizes the CD40/CD40L interaction. Typically these moieties will be CD40 agonistic antibodies or agonistic CD40L polypeptides. As discussed, these antibodies include by way of example human antibodies, chimeric antibodies, humanized antibodies, bispecific antibodies, scFvs, and antibody fragments that specifically agonize the CD40/CD40L binding interaction. Most preferably the antibody will comprise a chimeric, fully human or humanized CD40 antibody.

Human CD40L and other mammalian CD40L polypeptides are widely known and available including soluble forms thereof, oligomeric CD40L polypeptides such as trimeric CD40L originally reported by Immunex (now Amgen). Also, the sequence of human and murine CD40L is known and is commercially available. (See Immunex patents incorporated by reference supra). As noted above the CD40L dose will typically be at least 0.1 mg/kg/day and more typically from at least about 0.15 to 1.0 mg/kg/day. The MTD will be selected such that adverse side effects such as liver toxicity and increased liver transaminase levels are not observed or are minimized or negligible relative to when the CD40L polypeptide is administered in the absence of the type 1 interferon or a TLR agonist.

As noted, the type 1 interferon can be any type 1 interferon or variant or fragment that elicits a synergistic effect on cellular immunity when administered proximate to or in combination with a CD40 agonist. Such interferons may include alpha interferon, beta interferon, interferon taus such as tau 1, 2, 3, 4, 5, 6, 7, 8, 9 or 10, interferon omega, interferon epsilon, interferon zeta and the like, especially variants and fragments thereof. This especially includes PEGylated interferons and consensus interferons and interferons with altered (non-native or aglycosylated) glycosylation.

While it has been previously reported by the inventors and others that TLR agonists synergize with anti-CD40 agonists resulting in a profound enhancement of CD8+ T cell immunity; these prior studies would not have suggested that a type 1 interferon and a CD40 agonist such as an agonistic antibody would also yield synergistic effects on cellular immunity. Surprisingly, the inventors have discovered that the CD40 pathway is integrated with both the TLR and type 1 IFN signaling pathways for the induction of DC activation potent cellular immunity. Further, these earlier studies did not reveal the role of CD70 in this process.

Also, the prior studies would not have suggested the subject DNA or polypeptide conjugates since the prior studies involving TLR agonist/CD40 agonist combinations have required the separate administration of the antigen, the TLR agonist and the CD40 agonist. By contrast this invention in some embodiments provides DNA constructs and bipartite or tripartite polypeptides that comprise two or three different moieties or a DNA encoding these two or three moieties in a single DNA or polypeptide molecule, e.g., a conjugate containing a CD40 agonistic antibody, alpha interferon and an antigen. This should simplify the use thereof for prophylactic or therapeutic vaccine purposes and or for enhancing cellular immunity in the treatment of diseases wherein enhanced cellular immunity is desired such as cancer or autoimmune condition (since only one molecular entity will need to be formulated in pharmaceutically acceptable form and administered). This is particularly advantageous in the context of treatment of a chronic diseases or conditions wherein large amounts of adjuvant may be required for effective prophylactic or therapeutic immunity.

Combined IFN/CD40 agonist immunization, using only molecular reagents, uniquely generates CD8+ T cell responses of a magnitude that were previously only obtainable after challenge with an infectious agent (Ahonen et al., J Exp Med 199:775 (2004)). Thus, this invention provides for the development of potent vaccines against HIV and other chronic infectious diseases involving viruses, bacteria, fungi or parasites as well as proliferative diseases such as cancer, autoimmune diseases, allergic disorders, and inflammatory diseases where effective treatment requires the quantity and quality of cellular immunity that only combined IFN (type 1)/CD40 agonist immunization or other adjuvant combinations that upregulate CD70 expression on dendritic cells is capable of generating.

Applications of the Invention

The invention exemplifies herein both protein and DNA based vaccines comprising the combination of (i) at least one CD40 agonist, e.g., an agonistic anti-CD40 ab or CD40L polypeptide, (ii) optionally at least one target antigen (e.g., HIV Gag) and (iii) at least one Type 1 Interferon (e.g. alpha interferon). HIVGag40 is an appropriate model antigen because HIV is a chronic infectious disease wherein an enhanced cellular immune response has significant therapeutic potential. However, the invention embraces the construction of conjugates as described containing any antigen against which an enhanced cellular immune response is therapeutically desirable. In a preferred embodiment at least one target antigen is comprised in the administered composition containing at least one type 1 interferon, and at least one CD40 agonist or is contained in a polypeptide conjugate containing these moieties or is encoded by a DNA conjugate encoding these moieties. However, in some embodiments a conjugate containing type 1 interferon and the anti-CD40 antibody may be administered separate from the antigen, or the host may be naturally exposed to the antigen. Additionally, in some embodiments all three moieties, i.e., the anti-CD40 antibody, the type 1 interferon and the antigen may be co-administered as separate discrete entities. Preferably all these moieties are administered substantially concurrently in order to achieve the desired synergistic enhancement in cellular immunity without adverse side effects such as liver toxicity, venous thromboembolism, cytokine toxicity, and/or headache. However, these moieties may be administered in any order that elicits a synergistic effect on cellular immunity resulting in enhanced CD8+ T cell expansion and induction of CD70 expression on CD8+ DCs.

Exemplary antigens include but are not limited to bacterial, viral, parasitic, allergens, autoantigens and tumor associated antigens. If a DNA based vaccine is used the antigen will typically be encoded by a sequence the administered DNA construct. Alternatively, if the antigen is administered as a conjugate the antigen will typically be a protein comprised in the administered conjugate. Still further, if the antigen is administered separately from the CD40 agonist and the type 1 interferon moieties the antigen can take any form. Particularly, the antigen can include protein antigens, peptides, whole inactivated organisms, and the like.

Specific examples of antigens that can be used in the invention include antigens from hepatits A, B, C or D, influenza virus, *Listeria, Clostridium botulinum*, tuberculosis, tularemia, Variola major (smallpox), viral hemorrhagic fevers, *Yersinia pestis* (plague), HIV, herpes, pappilloma virus, and other antigens associated with infectious agents. Other antigens include antigens associated with a tumor cell, antigens associated with autoimmune conditions, allergy and asthma. Administration of such an antigen in conjunction with the subject agonist combination type 1 interferon and an anti-CD40 antibody can be used in a therapeutic or prophylactic vaccine for conferring immunity against such disease conditions.

In some embodiments the methods and compositions can be used to treat an individual at risk of having an infection or has an infection by including an antigen from the infectious agent. An infection refers to a disease or condition attributable to the presence in the host of a foreign organism or an agent which reproduce within the host. A subject at risk of having an infection is a subject that is predisposed to develop an infection. Such an individual can include for example a subject with a known or suspected exposure to an infectious organism or agent. A subject at risk of having an infection can also include a subject with a condition associated with impaired ability to mount an immune response to an infectious agent or organism, for example a subject with a congenital or acquired immunodeficiency, a subject undergoing radiation or chemotherapy, a subject with a burn injury, a subject with a traumatic injury, a subject undergoing surgery, or other invasive medical or dental procedure, or similarly immunocompromised individual.

Infections which may be treated or prevented with the vaccine compositions of this invention include bacterial, viral, fungal, and parasitic. Other less common types of infection also include are rickettsiae, mycoplasms, and agents causing scrapie, bovine spongiform encephalopathy (BSE), and prion diseases (for example kuru and Creutzfeldt-Jacob disease). Examples of bacteria, viruses, fungi, and parasites that infect humans are well know. An infection may be acute, subacute, chronic or latent and it may be localized or systemic. Furthermore, the infection can be predominantly intracellular or extracellular during at least one phase of the infectious organism's agent's life cycle in the host.

Bacteria infections against which the subject vaccines and methods may be used include both Gram negative and Gram positive bacteria. Examples of Gram positive bacteria include but are not limited to *Pasteurella* species, *Staphylococci* species, and *Streptococci* species. Examples of Gram negative bacteria include but are not limited to *Escherichia coli, Pseudomonas* species, and *Salmonella* species. Specific examples of infectious bacteria include but are not limited to *Heliobacter pyloris, Borrelia burgdorferi, Legionella pneumophilia, Mycobacteria* spp. (for example *M. tuberculosis, M. avium, M. intracellilare, M. kansaii, M. gordonae), Staphylococcus aureus, Neisseria gonorrhoeae, Neisseria meningitidis, Listeria monocytogeners, Streptococcus pyogenes*, (group A *Streptococcus*), *Streptococcus agalactiae*(Group B *Streptococcus*), *Streptococcus* (viridans group), *Streptococcus faecalis, streptococcus bovis, Streptococcus* (aenorobic spp.), *Streptococcus pneumoniae*, pathogenic *Campylobacter* spp., *Enterococcus* spp., *Haemophilus influenzae, Bacillus anthracis, Corynebacterium diptheriae, Corynebacterium* spp., *Erysipelothrix rhusiopathie, Clostridium perfringens, Clostridium tetani, Enterobacter aerogenes, Klebsiella pneumoniae, Pasteurella multocida, Bacteroides* spp., *Fusobacterium nucleatum, Streptobacillus moniliformis, Treponema pallidum, Treponema pertenue, Leptospira, Rickettsia*, and *Actinomyces israelii*.

Examples of viruses that cause infections in humans include but are not limited to Retroviridae (for example human deficiency viruses, such as HIV-1 (also referred to as HTLV-III), HIV-II, LAC or IDLY-III/LAV or HIV-III and other isolates such as HIV-LP, Picornaviridae (for example poliovirus, hepatitis A, enteroviruses, human Coxsackie viruses, rhinoviruses, echoviruses), Calciviridae (for example strains that cause gastroenteritis), Togaviridae (for example equine encephalitis viruses, rubella viruses), Flaviviridae (for example dengue viruses, encephalitis viruses, yellow fever viruses) Coronaviridae (for example coronaviruses), Rhabdoviridae (for example vesicular stomata viruses, rabies viruses), Filoviridae (for example Ebola viruses) Paramyxoviridae (for example parainfluenza viruses, mumps viruses, measles virus, respiratory syncytial virus), Orthomyxoviridae (for example influenza viruses), Bungaviridae (for example Hataan viruses, bunga viruses, phleoboviruses, and Nairo viruses), Arena viridae (hemorrhagic fever viruses), Reoviridae (for example reoviruses, orbiviruses, rotaviruses), Bimaviridae, Hepadnaviridae (hepatitis B virus), Parvoviridae (parvoviruses), Papovaviridae (papilloma viruses, polyoma viruses), Adenoviridae (adenoviruses), Herpeviridae (for example herpes simplex virus (HSV) I and II, varicella zoster virus, pox viruses) and Iridoviridae (for example African swine fever virus) and unclassified viruses (for example the etiologic agents of Spongiform encephalopathies, the agent of delta hepatitis, the agents of non-A, non-B hepatitis (class 1 enterally transmitted; class 2 parenterally transmitted such as Hepatitis C); Norwalk and related viruses and astroviruses).

Examples of fungi include *Aspergillus* spp., *Coccidoides immitis, Cryptococcus neoformans, Candida albicans* and other *Candida* spp., *Blastomyces dermatidis, Histoplasma capsulatum, Chlamydia trachomatis, Nocardia* spp., and *Pneumocytis carinii*.

Parasites include but are not limited to blood-borne and/or tissue parasites such as *Babesia microti, Babesi divergans, Entomoeba histolytica, Giarda lamblia, Leishmania tropica, Leishmania* spp., *Leishmania braziliensis, Leishmania donovdni, Plasmodium falciparum, Plasmodium malariae, Plasmodium ovale, Plasmodium vivax, Toxoplasma gondii, Trypanosoma gambiense* and *Trypanosoma rhodesiense* (African sleeping sickness), *Trypanosoma cruzi* (Chagus' disease) and *Toxoplasma gondii*, flat worms, and round worms.

As noted this invention embraces the use of the subject synergistic combination or protein or DNA conjugates containing or encoding this synergistic combination in treating proliferative diseases such as cancers. Cancer is a condition of uncontrolled growth of cells which interferes with the normal functioning of bodily organs and systems. A subject that has a cancer is a subject having objectively measurable cancer cells present in the subjects' body. A subject at risk of developing cancer is a subject predisposed to develop a cancer, for example based on family history, genetic predisposition, subject exposed to radiation or other cancer-causing agent. Cancers which migrate from their original location and seed vital organs can eventually lead to the death of the subject through the functional deterioration of the affected organ. Hematopoietic cancers, such as leukemia, are able to out-compete the normal hematopoietic compartments in a subject thereby leading to hematopoietic failure (in the form of anemia, thrombocytopenia and neutropenia), ultimately causing death.

A metastasis is a region of cancer cells, distinct from the primary tumor location, resulting from the dissemination of cancer cells from the primary tumor to other parts of the body. At the time of diagnosis of the primary tumor mass, the subject may be monitored for the presence of metastases. Metastases are often detected through the sole or combined use of magnetic resonance imaging (MRI), computed tomography (CT), scans, blood and platelet counts, liver function studies, chest-X-rays and bone scans in addition to the monitoring of specific symptoms.

The compositions, protein conjugates and DNA vaccines of the invention can be used to treat a variety of cancers or subjects at risk of developing cancer, including CD40 expressing and non-expressing cancers by the inclusion of a tumor-associated-antigen (TAA), or DNA encoding. This is an antigen expressed in a tumor cell. Examples of such cancers include breast, prostate, lung, ovarian, cervical, skin, melanoma, colon, stomach, liver, esophageal, kidney, throat, thyroid, pancreatic, testicular, brain, bone and blood cancers such as leukemia, chronic lymphocytic leukemia, and the like. The vaccination methods of the invention can be used to stimulate an immune response to treat a tumor by inhibiting or slowing the growth of the tumor or decreasing the size of the tumor. A tumor associated antigen can also be an antigen expressed predominantly by tumor cells but not exclusively.

Additional cancers include but are not limited to basal cell carcinoma, biliary tract cancer, bladder cancer, bone cancer, brain and central nervous system (CNS) cancer, cervical cancer, choriocarcinoma, colorectal cancers, connective tissue cancer, cancer of the digestive system, endometrial cancer, esophageal cancer, eye cancer, head and neck cancer, gastric cancer, intraepithelial neoplasm, kidney cancer, larynx cancer, liver cancer, lung cancer (small cell, large cell), lymphoma including Hodgkin's lymphoma and non-Hodgkin's lymphoma; melanoma; neuroblastoma; oral cavity cancer (for example lip, tongue, mouth and pharynx); ovarian cancer; pancreatic cancer; retinoblastoma; rhabdomyosarcoma; rectal cancer; cancer of the respiratory system; sarcoma; skin cancer; stomach cancer; testicular cancer; thyroid cancer; uterine cancer; cancer of the urinary system; as well as other carcinomas and sarcomas.

The compositions, protein conjugates, and DNA s of the invention can also be used to treat autoimmune diseases such as multiple sclerosis, rheumatoid arthritis, type 1 diabetes, psoriasis or other autoimmune disorders. Other autoimmune disease which potentially may be treated with the vaccines and immune adjuvants of the invention include Crohn's disease and other inflammatory bowel diseases such as ulcerative colitis, systemic lupus eythematosus (SLE), autoimmune encephalomyelitis, myasthenia gravis (MG), Hashimoto's thyroiditis, Goodpasture's syndrome, pemphigus, Graves disease, autoimmune hemolytic anemia, autoimmune thrombocytopenic purpura, scleroderma with anti-collagen antibodies, mixed connective tissue disease, polypyositis, pernicious anemia, idiopathic Addison's disease, autoimmune associated infertility, glomerulonephritis) for example crescentic glomerulonephritis, proliferative glomerulonephritis), bullous pemphigoid, Sjogren's syndrome, psoriatic arthritis, insulin resistance, autoimmune diabetes mellitus (type 1 diabetes mellitus; insulin dependent diabetes mellitus), autoimmune hepatitis, autoimmune hemophilia, autoimmune lymphoproliferative syndrome (ALPS), autoimmune hepatitis, autoimmune hemophilia, autoimmune lymphoproliferative syndrome, autoimmune uveoretinitis, and Guillain-Bare syndrome. Recently, arteriosclerosis and Alzheimer's disease have been recognized as autoimmune diseases. Thus, in this embodiment of the invention the antigen will be a self-antigen against which the host elicits an unwanted immune response that contributes to tissue destruction and the damage of normal tissues.

The compositions, protein conjugates and DNA vaccines of the invention can also be used to treat asthma and allergic and inflammatory diseases. Asthma is a disorder of the respiratory system characterized by inflammation and narrowing of the airways and increased reactivity of the airways to inhaled agents. Asthma is frequently although not exclusively associated with atopic or allergic symptoms. Allergy is acquired hypersensitivity to a substance (allergen). Allergic conditions include eczema, allergic rhinitis, or coryza, hay fever, bronchial asthma, urticaria, and food allergies and other atopic conditions. An allergen is a substance that can induce an allergic or asthmatic response in a susceptible subject. There are numerous allergens including pollens, insect venoms, animal dander, dust, fungal spores, and drugs.

Examples of natural and plant allergens include proteins specific to the following genera: *Canine, Dermatophagoides, Felis, Ambrosia, Lotium, Cryptomeria, Alternaria, Alder, Alinus, Betula, Quercus, Olea, Artemisia, Plantago, Parietaria, Blatella, Apis, Cupressus, Juniperus, Thuya, Chamaecyparis, Periplanet, Agopyron, Secale, Triticum, Dactylis, Festuca, Poa, Avena, Holcus, Anthoxanthum, Arrhenatherum, Agrostis, Phleum, Phalaris, Paspalum, Sorghum*, and *Bromis*.

It is understood that the compositions, protein conjugates and DNA vaccines of the invention can be combined with other therapies for treating the specific condition, e.g., infectious disease, cancer or autoimmune condition. For example in the case of cancer the inventive methods may be combined with chemotherapy or radiotherapy.

Methods of making compositions as vaccines are well known to those skilled in the art. The effective amounts of the protein conjugate or DNA can be determined empirically, but can be based on immunologically effective amounts in animal models. Factors to be considered include the antigenicity, the formulation, the route of administration, the number of immunizing doses to be administered, the physical condition, weight, and age of the individual, and the like. Such factors are well known to those skilled in the art and can be determined by those skilled in the art (see for example Paoletti and McInnes, eds., Vaccines, from Concept to Clinic: A Guide to the Development and Clinical Testing of Vaccines for Human Use CRC Press (1999). As disclosed herein it is understood that the subject DNAs or protein conjugates can be administered alone or in conjunction with other adjuvants. Additionally, the subject adjuvants can be added to or administered in conjunction with existing vaccines in order to potentiate their efficacy. For example, these adjuvants may be used to potentiate the efficacy of viral vaccines such as the recently approved HPV vaccine for cervical cancer. Also, they may be combined with other adjuvants.

The DNAs and protein conjugates of the invention can be administered locally or systemically by any method known in the art including but not limited to intramuscular, intravenous, intradermal, subcutaneous, intraperitoneal, intranasal, oral or other mucosal routes. Additional routes include intracranial (for example intracisternal, or intraventricular), intraorbital, ophthalmic, intracapsular, intraspinal, and topical administration. The adjuvants and vaccine compositions of the invention can be administered in a suitable, nontoxic pharmaceutical carrier, or can be formulated in microcapsules or a sustained release implant. The immunogenic compositions of the invention can be administered multiple times, if desired, in order o sustain the desired cellular immune response. The appropriate route, formulation, and immunization schedule can be determined by one skilled in the art.

In the methods of the invention, in some instances the antigen and a Type 1 IFN/CD40 agonist conjugate may be administered separately or combined in the same formulation. In some instances it may be useful to include several antigens. These compositions may be administered separately or in combination in any order that achieve the desired synergistic enhancement of cellular immunity. Typically, these compositions are administered within a short time of one another, i.e. within about several days or hours of one another, most typically within about a half hour to an hour to facilitate the treatment regimen.

In some instances, it may be beneficial to include a moiety in the conjugate or the DNA which facilitates affinity purification. Such moieties include relatively small molecules that do not interfere with the function of the polypeptides in the conjugate. Alternatively, the tags may be removable by cleavage. Examples of such tags include poly-histidine tags, hemagglutinin tags, maltase binding protein, lectins, glutathione-S transferase, avidin and the like. Other suitable affinity tags include FLAG, green fluorescent protein (GFP), myc, and the like.

The subject adjuvant combinations and protein or DNA conjugates will be administered with a physiologically acceptable carrier such as physiological saline. The composition may also include another carrier or excipient such as buffers, such as citrate, phosphate, acetate, and bicarbonate, amino acids, urea, alcohols, ascorbic acid, phospholipids, proteins such as serum albumin, ethylenediamine tetraacetic acid, sodium chloride or other salts, liposomes, mannitol, sorbitol, glycerol and the like. The agents of the invention can be formulated in various ways, according to the corresponding route of administration. For example, liquid formulations can be made for ingestion or injection, gels or procedures can be made for ingestion, inhalation, or topical application. Methods for making such formulations are well known and can be found in for example, "Remington's Pharmaceutical Sciences," 18$^{th}$ Ed., Mack Publishing Company, Easton Pa.

As noted the invention embraces DNA based vaccines. These DNAs may be administered as naked DNAs, or may be comprised in an expression vector. Furthermore, the subject nucleic acid sequences may be introduce into a cell of a graft prior to transplantation of the graft. This DNA preferably will be humanized to facilitate expression in a human subject.

The subject polypeptide conjugates may further include a "marker" or "reporter". Examples of marker or reporter molecules include beta lactamase, chloramphenicol acetyltransferase, adenosine deaminase, aminoglycoside phosphotransferase, dihydrofolate reductase, hygromycin B-phosphotransferase, thymidine kinase, lacZ, and xanthine guanine phosphoribosyltransferase et al.

The subject nucleic acid constructs can be contained in any vector capable of directing its expression, for example a cell transduced with the vector. The inventors exemplify herein a baculovirus vector as they have much experience using this vector. Other vectors which may be used include T7 based vectors for use in bacteria, yeast expression vectors, mammalian expression vectors, viral expression vectors, and the like. Viral vectors include retroviral, adenoviral, adeno-associated vectors, herpes virus, simian virus 40, and bovine papilloma virus vectors.

Prokaryotic and eukaryotic cells that can be used to facilitate expression of the subject polypeptide conjugates include by way of example microbia, plant and animal cells, e.g., prokaryotes such as *Escherichia coli, Bacillus subtilis*, and the like, insect cells such as Sf21 cells, yeast cells such as *Saccharomyces, Candida, Kluyveromyces, Schizzosaccharomyces*, and *Pichia*, and mammalian cells such as COS, HEK293, CHO, BHK, NIH 3T3, HeLa, and the like. One skilled in the art can readily select appropriate components for a particular expression system, including expression vector, promoters, selectable markers, and the like suitable for a desired cell or organism. The selection and use of various expression systems can be found for example in Ausubel et al., "Current Protocols in Molecular Biology, John Wiley and Sons, New York, N.Y. (1993); and Pouwels et al., Cloning Vectors: A Laboratory Manual": 1985 Suppl. 1987). Also provided are eukaryotic cells that contain and express the subject DNA constructs.

In the case of cell transplants, the cells can be administered either by an implantation procedure or with a catheter-mediated injection procedure through the blood vessel wall. In some cases, the cells may be administered by release into the vasculature, from which the cells subsequently are distributed by the blood stream and/or migrate into the surrounding tissue.

The subject polypeptide conjugates or the DNA constructs contain or encode an agonistic anti-CD40 antibody or CD40L or fragment thereof that specifically binds or agonizes the binding of CD40 and CD40L, preferably murine or human CD40. As used herein, the term "antibody" is used in its broadest sense to include polyclonal and monoclonal antibodies, as well as antigen binding fragments thereof. This includes for example Fab, F(ab')2, Fd and Fv fragments.

In addition the term "antibody" includes naturally antibodies as well as non-naturally occurring antibodies such as single chain antibodies, chimeric antibodies, bifunctional and humanized antibodies. Preferred for use in the invention are chimeric, humanized and fully human antibodies. Methods for synthesis of chimeric, humanized, CDR-grafted, single chain and bifunctional antibodies are well known to those skilled in the art. In addition, agonistic antibodies specific to CD40 are widely known and available and can be made by immunization of a suitable host with a CD40 antigen, preferably human CD40.

The use of an anti-mouse CD40 antibody (FGK45) is exemplified in the examples. This antibody was selected because anti-human CD40 antibodies do not specifically bind murine CD40 and the in vivo studies were in rodents. In the case of human therapy the selected agonistic CD40 antibody will specifically bind human CD40. Agonistic CD40 antibodies specific to human CD40 are also known in the art and may be produced by known methods. Alternatively, the CD40 agonist may comprise a fragment of CD40L or a fusion protein containing that agonizes the interaction of human CD40 and CD40L.

As noted the synergistic combinations of the invention contain at least one type 1 interferon or a fragment or variant thereof that synergizes with a CD40 agonist to induce CD70 expression on CD8+ DCs and elicit potent expansion of CD8+ T cells in vivo. This includes by way of example alpha interferon, beta interferon, omega interferon, tao interferon, zeta interferon and epsilon interferon, et al as well as functional variants and fragments thereof.

It is understood that modifications which do not substantially affect the activity of the various embodiments of this invention are also provided within the definition of the invention provided herein.

Inventors' Rationale

As discussed above, all TLR agonists tested to date synergize with anti-CD40 for the induction of $CD8^+$ T cell immunity. However, it was observed that some TLR agonist/anti-CD40 combinations (for TLRs 3, 7, 9) display a profound dependence upon type I interferon ($IFN\alpha\beta$) for enhancing $CD8^+$ T cell expansion whereas other TLR/CD40 agonist combinations (for TLRs 2 and 5) do not. Surprisingly, the depletion of CD4 cells eliminates the $IFN\alpha\beta$ requirement for generating $CD8^+$ T cell responses from TLR3- or -7/CD40-agonist combinations. Collectively these data suggested to the inventors a role for both $IFN\alpha\beta$ and CD4 cells in regulating the $CD8^+$ T cell response following combined TLR/CD40-agonist immunization.

Based on these observations, the inventors hypothesized that the induction of TNF ligand(s) on DCs is either dependent or independent of $IFN\alpha\beta$, and that this determines the subsequent dependency of the $CD8^+$ T cell response on $IFN\alpha\beta$. Because the $IFN\alpha\beta$-dependent $CD8^+$ T cell response can be recovered by CD4 depletion, it was hypothesized that either the expression of CD70 on DCs, or the CD8+ T cell response, is negatively influenced by regulatory T cells. We thereby proposed a mechanism whereby $IFN\alpha\beta$, following combined TLR (3, 7, or 9)/CD40-agonist immunization, influences the $CD8^+$ T cell response by performing one or more of the following functions: i) directly augmenting the $CD8^+$ T cell response to CD70-bearing APCs (CD8 T cell centric), ii) directly activating DCs for TNF ligand expression (DC centric), iii) inhibiting regulatory $CD4^+$ T cell activity against either APC TNF ligand expression or of CD8+ T cell expansion (Treg centric). Synergistic activity with anti-CD40 in the induction of $CD8^+$ T cell expansion is a property of all TLR agonists examined which now includes agonists for TLRs 1/2, 2/6, 3, 4, 5, 7, and 9. Collectively, these data demonstrate that combined TLR/CD40-agonist immunization can reconstitute all of the signals required to elicit potent primary $CD8^+$ T cell responses.

To determine the cellular and molecular requirements of the synergy between the TLRs and CD40, numerous experiments were performed in knockout and/or mice depleted of various cell types or factors by blocking or depletion with antibodies. These studies confirmed the necessity of intact CD40 and TLR signaling pathways (using CD40 KO and MyD88 KO mice). Though this synergy was not dependent on CD4 cells, IFNγ, IL-12, or IL-23, observed was a variable dependence of the synergy on $IFN\alpha\beta$ depending on the TLR agonist used. Ahonen, C. L., C. L. Doxsee, S. M. McGurran, T. R. Riter, W. F. Wade, R. J. Barth, J. P. Vasilakos, R. J. Noelle, and R. M. Kedl. 2004. Combined TLR and CD40 triggering induces potent CD8+ T cell expansion with variable dependence on type I IFN. *J Exp Med* 199:775. It was observed that the degree of dependence on $IFN\alpha\beta$ generally seemed to correlate with the amount of $IFN\alpha\beta$ the given TLR induced. Thus, $IFN\alpha\beta$ receptor knockout ($IFN\alpha\beta R$ KO) mice immunized with anti-CD40 in combination with an agonist for TLR 3, 7, or 9 failed to generate a $CD8^+$ T cell response. Conversely, $IFN\alpha\beta R$ KO mice immunized with anti-CD40 in combination with an agonist for TLR 2 or 5 did generate a $CD8^+$ T cell response. These data suggested to the inventors that $IFN\alpha\beta$ potentially can play a much larger role in generating adaptive immunity than has been previously appreciated as shown in the examples which follow.

At the outset it should be emphasized that the precise role of $IFN\alpha\beta$ in the generation of T cell responses was difficult to predict and clarify. This difficulty is due in part to the fact that many of the effects of $IFN\alpha\beta$ on T cell function appear to be indirect. $IFN\alpha\beta$ enhances numerous aspects of APC activation, including the elevation of MHC molecules on the majority of cell types. Tough, D. F. 2004. Type I interferon as a link between innate and adaptive immunity through dendritic cell stimulation. *Leuk Lymphoma* 45:257; Le Bon, A., and D. F. Tough. 2002. Links between innate and adaptive immunity via type I interferon. *Curr Opin Immunol* 14:432. More recently, $IFN\alpha\beta$ has been shown to promote APC processing of exogenous antigen into the class I pathway, a process known as cross-priming. Le Bon, A., N. Etchart, C. Rossmann, M. Ashton, S. Hou, D. Gewert, P. Borrow, and D. F. Tough. 2003. Cross-priming of CD8+ T cells stimulated by virus-induced type I interferon. *Nat Immunol* 4:1009. This allows the generation of $CD8^+$ T cell responses after the administration of exogenous protein antigen. $IFN\alpha\beta$ also has other effects on T cell activation and proliferation. High levels of $IFN\alpha\beta$ also induce partial activation of naïve, and proliferation of memory, CD8 T cells. Tough, D. F., S. Sun, X. Zhang, and J. Sprent. 1999. Stimulation of naive and memory T cells by cytokines. *Immunol Rev* 170:39' Sprent, J., X. Zhang, S. Sun, and D. Tough. 2000. T-cell proliferation in vivo and the role of cytokines. *Philos Trans R Soc Lond B Biol Sci* 355:317; Sprent, J. 2003. Turnover of memory-phenotype CD8+ T cells. *Microbes Infect* 5:227; Zhang, X., S. Sun, I. Hwang, D. F. Tough, and J. Sprent. 1998. Potent and selective stimulation of memory-phenotype CD8+ T cells in vivo by IL-15. *Immunity* 8:591; Tough, D. F., and J. Sprent. 1998. Bystander stimulation of T cells in vivo by cytokines. *Vet Immunol Immunopathol* 63:123.

The effects of $IFN\alpha\beta$ on naïve T cells may in part be mediated through APCs, although $IFN\alpha\beta$ directly stimulates naïve T cell survival. Marrack, P., J. Kappler, and T. Mitchell. 1999. Type I interferons keep activated T cells alive. *J Exp Med* 189:521; Marrack, P., T. Mitchell, J. Bender, D. Hildeman, R. Kedl, K. Teague, and J. Kappler. 1998. T-cell survival. *Immunol Rev* 165:279. This survival activity is dependent on STAT1 in the T cells, indicating that direct $IFN\alpha\beta$ signaling in the T cells must be involved. Marrack, P., J. Kappler, and T. Mitchell. 1999. Type I interferons keep activated T cells alive. *J Exp Med* 189:521. More recently, $IFN\alpha$ has been show to act directly on naïve $CD8^+$ T cells, in concert with antigen and B7-mediated co-stimulation, to facilitate proliferation, effector function and development of memory Curtsinger, J. M., J. O. Valenzuela, P. Agarwal, D. Lins, and M. F. Mescher. 2005.

Type I IFNs provide a third signal to CD8 T cells to stimulate clonal expansion and differentiation. *J Immunol* 174: 4465. By contrast, others have demonstrated that the influence of IFNαβ on the proliferation of CD8+ memory T cells is indirect. This proliferation occurs via production of IL-15 from other cell types, and selectively induces proliferation of memory CD8 but not CD4 T cells. Zhang, X., S. Sun, I. Hwang, D. F. Tough, and J. Sprent. 1998. Potent and selective stimulation of memory-phenotype CD8+ T cells in vivo by IL-15. *Immunity* 8:591; Sprent, J., X. Zhang, S. Sun, and D. Tough. 1999. T-cell turnover in vivo and the role of cytokines. *Immunol Lett* 65:21. Therefore in the initiation of T cell activation and proliferation, both indirect and direct effects of IFNαβ on T cells have been observed.

By contrast, there is little data on the influence of type I IFN on regulatory T cell development or function. One report demonstrated that human regulatory cells could be produced in vitro using a combination of IFNα and IL-10. Levings, M. K., R. Sangregorio, F. Galbiati, S. Squadrone, R. de Waal Malefyt, and M. G. Roncarolo. 2001. IFN-alpha and IL-10 induce the differentiation of human type 1 T regulatory cells. *J Immunol* 166:5530.

As described above and supported by the data in the examples which follow the inventive discovery that type 1 interferon and CD40 agonist combinations elicit a synergistic effect on cellular immunity and upregulate CD70 on dendritic cells and provide for exponential expansion of CD8+ T cells allows for the development of more potent vaccines against the kinds of diseases whose treatment seems to require the quantity and quality of cellular immunity that the subject novel adjuvant combinations elicit.

The following examples are offered for purposes of exemplification. It should be understood, however, that the scope of the present invention is defined by the claims.

Materials and Methods Used in Some of the Following Examples.

C57BL/6, IFNαβR KO, or CD4-depleted IFNαβR KO mice are immunized with a model antigen. Briefly, 0.1-0.5 mgs of whole protein (ovalbumin or HSV glycoprotein B [HSVgB]) or 50 ug of peptide (SIINFEKL for ovalbumin, SSIFFARL for HSVgB, TSYKSEFV for vaccinia virus B8R) is injected i.p. in combination with a TLR agonist (50 ug Pam3Cys, 25 µg MALP-2, 100 µg PolyIC, 150 µg 27609, 50 µg CpG 1826, or 25 µg flagellin), the anti-CD40 antibody FGK45 (50 µg), or both. Ovalbumin is purchased from Sigma Corporation (St. Louis, Mo.) and contaminating LPS removed using a TritonX-114 LPS-detoxification methodology as previously described. Adam, O., A. Vercellone, F. Paul, P. F. Monsan, and G. Puzo. 1995. A nondegradative route for the removal of endotoxin from exopolysaccharides. *Anal Biochem* 225:321. Whole HSVgB protein is made by expression in baculovirus and purification on a nickel column, as previously described and kindly provided by Dr. Roselyn Eisenberg from the University of Pennsylvania. Bender, F. C., J. C. Whitbeck, M. Ponce de Leon, H. Lou, R. J. Eisenberg, and G. H. Cohen. 2003. Specific association of glycoprotein B with lipid rafts during herpes simplex virus entry. *J Virol* 77:9542. The TLR agonists used are either purchased (Pam3Cys-InVivogen, MALP-2-Alexis Biochemicals, PolyIC—Amersham/GE Healthcare, CpG 1826-Invitrogen), provided through a material transfer agreement (27609-3M Pharmaceuticals), or synthesized in house (flagellin). Each TLR agonist has been tested for LPS contamination by Limulus assay and found to have less than 5 IU of LPS activity (approximately 50-300 ng) for the amounts injected in vivo. Injection of this amount of LPS has no observable effects on spleen dendritic cells in vivo (data not shown). In the case of the flagellin isolated in-house, contaminating LPS was removed using the same protocol as described above for ovalbumin detoxification.

These TLR agonists were chosen for use in our experiments for two main reasons. First, the major DC subsets in secondary lymphoid tissue are the CD8+ and CD11b+ DCs and they express both common and unique TLRs. The TLR agonists chosen directly stimulate either the CD8+ DC (polyIC-TLR3), the CD11b+ DC (27609-TLR7 and flagellin-TLR5), or both DC subsets (Pam3Cys/MALP-2, TLR2 stimulation). Second, the molecules selected represent TLR agonists that are either IFNαβ-dependent (poly IC, 27609, CpG 1826) or -independent (Malp-2, Pam3Cys, flagellin) for inducing CD8+ T cell responses in combination with anti-CD40.

The immunizations described are performed both with and without the co-administration of the antibodies blocking CD70 (FR70), OX40L/CD134 (RM134L), or 41BBL/CD137L (TKS-1). I.p. administration of 250 ug of antibody every 2 days is sufficient to block the interaction of each of these ligand/receptor interactions (See FIG. 5). Blocking experiments are performed using this regimen and later similar experiments used to determine the minimum amount of blocking antibody necessary to have an effect, if any, on the CD8+ T cell response.

To monitor the antigen-specific CD8+ T cell response, 5-7 days after immunization peripheral blood and/or spleen cells are isolated and stained with H-2K$^b$/SIINFEKL or H-2K$^b$/SSIFFARL MHC tetramers, as previously described. Kedl, R. M., M. Jordan, T. Potter, J. Kappler, P. Marrack, and S. Dow. 2001. CD40 stimulation accelerates deletion of tumor-specific CD8(+) T cells in the absence of tumor-antigen vaccination. *Proc Natl Acad Sci USA* 98:10811; Kedl, R. M., W. A. Rees, D. A. Hildeman, B. Schaefer, T. Mitchell, J. Kappler, and P. Marrack. 2000. T Cells Compete for Access to Antigen-bearing Antigen-presenting Cells. *J. Exp. Med.* 192:1105; Kedl, R. M., B. C. Schaefer, J. W. Kappler, and P. Marrack. 2002. T cells down-modulate peptide-MHC complexes on APCs in vivo. 3:27. The CD8+ T cells are analyzed by intracellular interferon γ (IC IFNγ) staining as an indicator of the cells' effector cytokine production capability. IC IFNγ staining has been extensively utilized in the literature and will be performed as described. In addition, CD107a expression after antigenic stimulation will be analyzed as an indication of antigen-specific lytic function. CD107a (LAMP-1) is a membrane protein constituent of lytic granules and its identification on the plasma membrane of T cells after antigenic stimulation is an indication of the exocytosis of lytic granules. Combined tetramer and CD107a staining is performed as previously described. Briefly, cells are incubated for 30 minutes with MHC tetramer at 37 degrees. Antigenic peptide (1 ug/ml) and anti-CD107a-FITC antibody are then added for another hour, after which 1 ug/ml monensin is added to the cells to inhibit the destruction of the FITC fluorescence as antibody bound CD107a is internalized into lysosomes. The cells are further incubated for another 3-4 hours at 37 degrees, stained with antibodies against CD8, washed, fixed and analyzed by FACS. As described above, IFNαβR KO mice are similarly injected with blocking antibodies to CD70, 41BBL, OX-40L, and CD30L during combined TLR2- or -5/CD40-agonist immunization. The magnitude and function of the CD8+ T cell response will be determined by tetramer and IC IFNγ staining and FACS analysis of PBLs and/or spleen cells as described above.

In order to determine the effects of TNF ligand blockade during the primary immunization on the development of memory CD8+ T cells, immunized mice are rested for at least 60 days, re-challenged with the same immunization, and the secondary response analyzed as described above. Experiments are performed in IFNαβR KO mice, CD4-depleted IFNαβR KO mice, and normal and CD4-depleted B6 mice as controls. The TLR/CD40 combinations that generate IFNαβ-independent CD8+ T cell responses are analyzed in the intact IFNαβR KO mice. Both IFNαβ-dependent and -independent TLR/CD40 combinations are tested in CD4-depleted IFNαβR KO mice. Representative CD4-depleted and immunized mice are rested for at least 60 days after primary immunization and then rechallenged by combined TLR/CD40-agonist immunization. These experiments are used to determine whether the primary and memory CD8+ T cell response following immunization of a IFNαβ-deficient host, CD4-depleted or not, is dependent on CD70 and/or other TNF ligands.

EXAMPLE 1

CD8+ T Cell Expansion Following Combined TLR/CD40-Agonist Immunization Demonstrates Variable Dependence Upon IFNαβ

While all TLR agonists synergized with anti-CD40 to promote CD8+ T cell expansion, the inventors observed that the CD8+ T cell responses elicited from certain TLR agonists/anti-CD40 combinations was completely dependent on IFNαβ. Based thereon the inventors immunized interferon αβ receptor knockout (IFNαβR KO) mice with peptide antigen in the context of different combined TLR/CD40-agonists in the experiments contained in FIGS. 1 and 2 as described above.

In the experiment contained in FIG. 1 CD8+ T cell expansion was measured following combined TLR/CD40 agonist administration in agonmice (bottom row) which were immunized with ovalbumin peptide, anti-CD40, and the indicated TLR agonists. Seven days later the ovalbumin-specific T cell responses were measured in the spleen by tetramer staining and FACS analysis. Numbers in the upper right quadrant indicate the percentage of tetramer staining cells out of total CD8+ cells.

In the experiment contained in FIG. 2 it was shown that CD4 depletion of IFN alphabetaR KO hosts restores the CD8+ T cell response following immunization with IFNalphabeta-dependent TLR agonist in combination with agonistic anti-CD40. WT and IFNalphabetaR KO mice, CD4 depleted or non-deleted as shown in FIG. 2, were immunized with HSV-1 peptide, agonistic anti-CD40-antibody, and poly IC. Seven days later the HSV-1 specific response was determined by tetramer (A) and IC IFNgamma (B) staining PBL cells.

As shown by the results contained in FIG. 2, the CD8+ T cell response to immunization with TLR 3, 7, or δ agonists in combination with anti-CD40 was completely abrogated in these mice (FIG. 2). By contrast, the CD8+ T cell response to the remaining TLR/CD40-agonist combinations was either only partially dependent (TLR4/CD40) or relative independent (TLR2/6/CD40-agonists) of IFNαβ (FIG. 1). In other experiments, the TLR1/2 agonist Pam3Cys and the TLR5 agonist flagellin also generated CD8+ T cell responses in IFNαβR KO comparable to wt mice when used in combination with anti-CD40 (data not shown). These results demonstrate that anti-CD40 in combination with a TLR 2 or δ agonist elicits IFNαβ-independent CD8+ T cell responses while anti-CD40 in combination with a TLR 3, 7, or δ agonist elicits IFNαβ-dependent CD8+ T cell responses. Thus, TLR 2 or 5-agonist synergy with the CD40 pathway can be considered IFNαβ-independent. Conversely, TLR 3, 7, or 9-agonist synergy with the CD40 pathway can be considered IFNαβ-dependent. This data suggested to the inventors a role for IFNαβ in the generation of CD8+ T cell responses by signaling through either the T cells directly, the antigen bearing APC, or both.

EXAMPLE 2

Figure 2A:
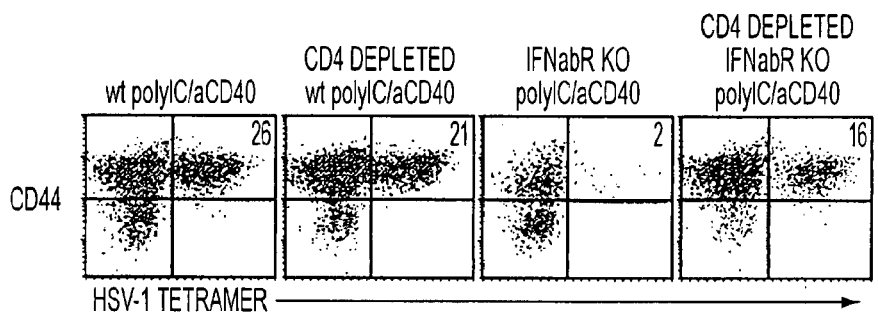
Figure 2B:
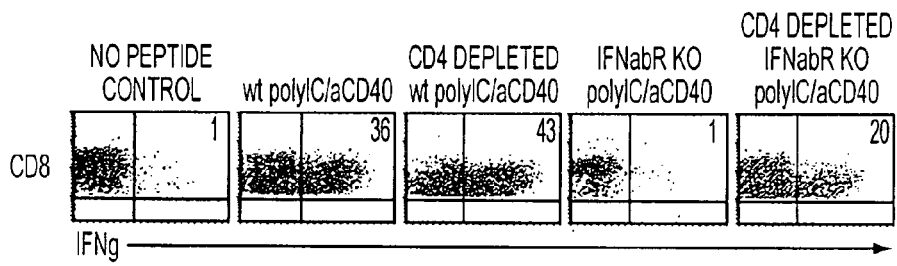

CD8+ T Cell Expansion Following Combined TLR/CD40-Agonist Immunization is Recovered in CD4-Depleted IFNαβR KO Hosts The deficient CD8+ T cell response in IFNαβR KO mice seemed to suggest to the inventors an obligate role for IFNαβ in the response elicited by certain TLR/CD40-agonist combinations described above. As shown in the experiment in FIG. 2, Wt and IFNαβR KO mice were depleted of CD4+ T cells by injection of the anti-CD4 antibody GK1.5 one day before peptide immunization in conjunction with combined TLR/CD40-agonists (FIG. 2). Seven days after combined TLR/CD40-agonist immunization, mice were sacrificed and PBL and spleen cells were isolated and analyzed by tetramer and intracellular IFNγ staining. Immunization with peptide and polyIC/anti-CD40 failed to generate a CD8+ T cell response in IFNαβR KO mice. However, CD4 depletion restored the CD8+ T cell response in IFNαβR KO mice with respect to both numbers (percent of total CD8+ T cells, FIG. 2A) and function (FIG. 2B) of antigen-specific T cells. This was true for all TLR/CD40-agonist combinations tested (TLRs, 2, 5 and 7) where even the CD8+ T cell response to IFNαβ-independent TLR/CD40-agonist combinations (i.e. TLR2) was enhanced compared to non-CD4-depleted controls (data not shown). Thus, the CD8+ T cell response in IFNαβR KO mice following combined TLR/CD40-agonist immunization is generally enhanced after CD4 depletion.

One concern the inventors had with these findings was whether or not they were physiologically relevant or were simply unique to the IFNαβR KO hosts. Therefore experiments were effected in wt hosts using a polyclonal rabbit anti-IFN antibody to block IFNαβ, with and without CD4 depletion.

As shown in FIG. 3 anti-IFN blocks polyIC/CD40 mediated CD8 responses which are recovered by CD4 depletion. In this experiment mice were immunized against ovalbumin (combined polyIC/anti-CD40) with and without anti-IFN and/or CD4 depletion. at day 7 PBLs were analyzed by tetramer staining as described in the Materials and Methods above for the percent antigen-specific T cells.

As shown in FIG. 3, for wt mice immunized with combined polyIC/aCD40, the anti-FNαβ antibody significantly reduced the magnitude of the CD8+ T cell response (FIG. 3). Consistent with the results seen in the IFNαβR KO mice, CD4 depletion of anti-IFN treated mice fully recovered the CD8+ T cell responses. Therefore, both in the IFNαβR KO hosts as well as in wt host injected with IFNαβ-depleting antibodies, CD4 depletion appeared to alleviate the dependency of the CD8+ T cell response on IFNαα following combined TLR/CD40-agonist immunization. These results suggested to the inventors 1) that a subpopulation of CD4+ T cells regulates the CD8+ T cell response in IFNαβR KO mice following immunization with certain TLR/CD40-agonist combinations, 2) that IFNαβ may play a role in inhibiting the regulatory ability of this population of CD4+ T cells following immunization with these TLR/CD40-agonist combinations, and 3) other TLR/CD40-agonist combinations (e.g. TLR2 or 5) are able to avoid inhibition by regulatory CD4+ T cells in a IFNαβ-independent fashion.

These results demonstrate that combined TLR/CD40-agonist immunization is able to elicit potent primary and secondary CD8+ T cell responses that display an intriguing variable dependence on IFNαβ depending upon the TLR agonist utilized. These findings suggested to the inventors a more direct role for IFNαβ in CD8+ T cell responses than has been previously appreciated. It was also shown that combined TLR/CD40 agonist immunization uniquely induces the upregulation of CD70 on DCs, upon which the ensuing CD8+ T cell response in WT mice appears to be largely dependent. This preliminary data suggested that the increased expression of CD70 on activated APCs, and the subsequent stimulation of antigen-specific T cells through CD27, is a primary checkpoint for the formation and survival of CD8+ T cell responses in response to combined TLR/CD40-agonist immunization. More surprising however is our observation that IFNαβ-dependent CD8+ T cell responses, in both IFNαβR KO (FIG. 2) and WT mice (FIG. 3), can be rescued by depleting the host of CD4+ T cells. These results suggested that IFNαβ may influence the CD8+ T cell response for the following reasons: 1) regulating the CD8+ T cell response to TNFL expressing APCs, 2) regulating APC activation and TNF ligand expression, 3) inhibiting CD4+ T cell regulatory function that suppresses either APC expression of TNF ligands or CD8+ T cell expansion to the TNFL-bearing APCs, 4) a combination of any of the above. The examples which follow conclusively determine the accuracy of these hypotheses by systematically examining i) the role of IFNαβ in mediating the CD8+ T cell response, ii) the role of IFNαβ in DC activation, and iii) the role of IFNαβ in CD4+ regulatory cell function, all following combined TLR/CD40-agonist immunization.

EXAMPLE 3

Role of TNF Ligands for the CD8+ Response in IFNαβR KOs

As shown in the experiment contained in FIG. 4, the CD8+ T cell response in WT mice generated by combined TLR/CD40-agonist immunization is dependent on CD70 (See FIG. 4). In this experiment the CD8+ T cell response was assayed in CD4-depleted IFNalphabetaR KO hosts following combined TLR/CD40 immunization and was shown from the results to be largely dependent on CD70. IFNalphabetaR KO mice were depleted of CD4 cells and immunized with HSV-1 peptide, polyIC, and anti-CD40 antibody as described above. Mice were then injected with anti-TNF ligand antibodies as in FIG. 1. At day seven PBLs were again analyzed by tetramer staining.

As shown in the foregoing experiments, the CD8+ T cell response in IFNαβR KO mice is unique in that it can only be elicited by TLR/CD40-agonist combinations that do not stimulate IFNαβ, or by CD4-depleting the IFNαβRKO host prior to TLR/CD40-agonist immunization. The results in FIG. 4 further indicate that CD70 plays a necessary role in the CD8+ T cell response in IFNαβR KO mice. It is noted that while anti-CD70 blocked the response by approximately 10-fold in this experiment, other TNFL antibodies inhibited the CD8+ T cell response only up to 2-fold. This suggests that, in contrast to wt mice (FIG. 1) multiple TNF ligands may have at least some influence on the magnitude of the CD8+ T cell response in IFNαβR KO mice. The data shown in FIG. 4 was achieved with minimal blocking antibody injected.

EXAMPLE 4

Materials and Methods

Injection of a soluble CD70/Ig fusion protein (sCD70Ig), originally described by Dr. Aymen Al-Shamkhani at Southampton General Hospital. (Rowley, T. F., and A. Al-Shamkhani. 2004. Stimulation by soluble CD70 promotes strong primary and secondary CD8+ cytotoxic T cell responses in vivo. J Immunol 172:6039), successfully provides an agonistic stimulus to T cells through CD27 in vivo. This reagent, kindly provided by Dr. Al-Shamkhani will be injected into IFNαβR KO hosts in combination with TLR and CD40 stimulation. Initially, we will attempt to rescue the CD8+ T cell response to IFNαβ-dependent TLR/CD40-agonist combinations by the additional injection of the sCD70Ig reagent. The CD8+ T cell response will again be analyzed on day 7 after initial antigen challenge. Data from Dr. Al-Shamkhani's laboratory have determined that daily injection of 250 ug sCD70Ig on days 2-4 after antigen challenge provide optimal CD70 mediated signals for CD8+ T cell expansion (personal communication). We have confirmed that this time course of sCD70Ig injection augments the CD8+ T cell response to a TLR agonist alone in WT mice (data not shown). Mice will be challenged i.p. on day 0 with antigen and a TLR agonist, anti-CD40, or both. On days two, three, and four after antigen injection, we will inject 250 ug of sCD70Ig i.p. and then analyze the CD8+ T cell response in the blood and/or spleen 7 days after the original antigen challenge.

From the data shown in FIG. 4, it is clear that CD4 depletion of IFNαβR KO hosts makes them responsive to any combination of TLR/CD40 stimulation. As shown in FIG. 4 CD70 blockade eliminates the synergy between the TLR agonist and the CD40 agonist for inducing a CD8+ T cell response. In the experiment mice were challenged with the indicated combinations of anti-CD40+/TLR- agonist. Representative subsets of mice were injected with the anti-CD70 blocking antibody FR70 (lower dot plots). FIG. 4A shows representative tetramer staining and FIG. 4B shows average and standard deviation of 3 mice per group and FIG. 4C shows where mice were immunized as in 5A but were given none, 1 or 2 injections of anti-CD70. DCs were isolated at 24 hours and analyzed for DC numbers (top panels) and CD70 staining (bottom panels) in each subset.

It can be seen that the CD8+ T cell response, in WT mice, following combined TLR/CD40-agonist immunization is dependent on CD70 (FIG. 4). The data described above and shown in FIG. 4 suggest that this is also true for at least CD4-depleted IFNαβR KO hosts. The results in FIG. 4 also suggest that multiple TNF ligands may participate, to one degree or another, in the CD8+ T cell response in IFNαβR KO hosts.

EXAMPLE 5

Immune Cell Response Following Recombinant Ifnα +/−Anti-CD40 in Wt Mice

Experiments were effected using the following materials and methods in order to determine whether the action of IFNαβ is alone sufficient for eliciting CD8+ T cell expansion following immunization with IFNαβ-dependent TLR/CD40-agonist combinations.

Materials and Methods.

Briefly, a novel IFNα sequence was cloned from polyIC-stimulated B cell cDNA. Of the induced subtypes, this IFNα subtype was selected because it has no glycosylation sequences and can therefore be expressed in insect cells without concern for aberrant glycosylation. A TCR Cα epitope tag was added to the C-terminus for affinity purification purposes and the sequence was cloned into the p10 promoter site of the pBac vector (Invitrogen). Recombinant baculovirus was produced and after infection of Hi5 cells, recombinant IFNα was purified from the supernatant by affinity and size chromatography. The activity of the IFNα was confirmed in vitro and in vivo based on the upregulation of class I MHC on APCs (data not shown).

The use of recombinant IFNα in a vaccine setting has been previously published (Le Bon, A., and D. F. Tough. 2002. Links between innate and adaptive immunity via type I interferon. *Curr Opin Immunol* 14:432) and a similar protocol will initially be used in the studies proposed here. Wild type mice are primed with antigen and anti-CD40 as described above in conjunction with $10^4$-$10^6$ units of IFNα. The resulting $CD8^+$ T cell response is then compared to mice immunize with combined TLR(3, 7, or 9)/CD40-agonists to determine if IFNα can synergize with anti-CD40 to the same degree as TLR stimulation for eliciting $CD8^+$ T cell expansion. Other control mice are injected with IFNα or anti-CD40 only. $CD8^+$ T cell responses are analyzed as described above.

As shown in the experiment contained in FIG. 5, the data obtained revealed that there is a synergistic effect on immunity with recombinant IFNα and anti-CD40. Mice were immunized with antigen in the context of 3 injections of $1 \times 10^5$ units IFN, a single injection of $1 \times 10^6$ units IFN, anti-CD40 alone, or anti-CD40 in conjunction with either dosing regimen of IFN. While IFN or CD40 alone stimulated a detectable CD8+ T cell response, the combined IFN/CD40 synergized to produce a CD8+ T cell response similar to that observed in response to polyIC/CD40 immunization (FIG. 5).

More particularly, this experiment reveals that the combined administration of type 1 interferon and an agonistic CD40 antibody induced an exponential expansion of antigen specific CD8+ and T cells compared to administration of either alone. Mice were injected i.p. with ovalbumin and the indicated combinations of anti-CD40, poly IC, or recombinant IFN. For IFN injections, mice were either given 3 consecutive daily injections of $1 \times 10^5$ units IFN, starting on the day of antigen injection, or a single injection of $1 \times 10^6$ units IFN at the same time of antigen injection. Seven days later, the mice were sacrificed and cells from either peripheral blood or spleen were stained with Tetramer to identify the magnitude of expansion of ovalbumin specific CD8+ T cells. The cells were analyzed by FACS and the data shown was gated on CD8+ B220-events. In the FIG. 5-(A) is the dot plates of tetramer staining and 5(B) is the average and standard deviation (from 2 individual mice) of two percent tetramer and CD8+ cell in the blood out of total CD8+ T cells.

The data contained in FIG. 5 reveals that recombinant type 1 interferon synergizes with CD40 to a similar degree as TLR/CD40 stimulation these results further demonstrate that the recombinant IFN produced in baculovirus works well in vivo. Moreover, these results reveal that combined IFNα/CD40 stimulation can synergize to a similar magnitude as TLR/CD40 stimulation in promoting CD8+ T cell expansion.

EXAMPLE 6

Combined Administration of Type 1 Interferon and CD40 Antibody Induce CD70+ Expression on DCs The data contained in the afore-described experiments suggests that IFNαβ-dependency is determined by the response of the DC and/or CD4+ Tregs to IFNαβ. The inventors hypothesized that CD70 is involved in the mechanism by which IFNαβ, in the context of combined IFNalpha/CD40-agonist immunization, elicits such potent $CD8^+$ T cell immunity. The results of the prior example particularly reveal that CD40 agonist and type 1 interferon elicit a synergistic effect on CD8+ immunity. (See FIG. 5). This data shows the eventual effect of combined IFNα/CD40 stimulation on the responding CD8+ T cells, not the APCs. The following experiments are conducted to examine whether combined IFNα/CD40 stimulation induces the expression of CD70 and/or other TNF ligands on antigen-bearing DC subsets.

Using the recombinant IFNα described above iWT B6 mice are primed with antigen and anti-CD40 as described above in conjunction with $10^4$-$10^6$ units of IFNα. As controls, mice are immunized with anti-CD40 alone, IFNα alone, or combined polyIC/anti-CD40 positive control for the increase in DC CD70 expression. Representative mice are sacrificed 6-48 hours after priming, the spleens collagenase digested, and the DCs stained and analyzed by FACS. The DCs are assessed for their expression of the TNF ligands CD70, 41BBL, OX-40L, CD30L, and GITRL. The resulting DC phenotype is compared to mice immunized with combined TLR3, 7, or 9/CD40-agonists to determine if IFNα can synergize with anti-CD40 to the same degree as TLR stimulation for eliciting $CD8^+$ T cell expansion. Other control mice will be injected with IFNα or anti-CD40 only. To determine the influence of IFNα on antigen processing and presentation of the various subsets, mice are challenged with fluorescent antigen as described above in conjunction with recombinant IFNα +/− anti-CD40. Antigen uptake, antigen presentation, and DC activation and TNFL expression are determined as described above. These experiments determine how IFNα, independently and in conjunction with anti-CD40, influences antigen presentation, DC TNFL expression, and $CD8^+$ T cell expansion.

As shown in the experiment contained in FIG. 6 the combined administration of type 1 interferon and an agonistic CD40 antibody induces CD70 expression on CD8+ T cells in vivo whereas the administration of either alone does not. In the experiment mice were injected with anti-CD40 antibody alone, polyIC (positive control), recombinant alpha interferon or anti-CD40 antibody and type 1 interferon. Eighteen hours later spleen DCs were isolated and analyzed for their expression of CD70. The numbers in the upper right quadrant of FIG. 7 indicate the mean fluorescent intensity of CD70 staining. This data also reveals that similar to polyIC/CD40 agonist administration, CD40/IFN similarly increases the expression of CD70 on CD8+ DCs.

Therefore, the data (FIG. 6) demonstrates the success of IFNα/CD40 immunization at eliciting a CD8+ T cell response and show that the DCs in IFNα/anti-CD40 injected mice are similar to DCs from combined TLR/CD40-agonist immunized controls with respect to antigen uptake, antigen presentation, and/or TNFL upregulation. Specifically, CD70 is increased on one or more DC subsets following combined IFNα/aCD40 immunization, though not with challenge of either stimulus alone.

EXAMPLE 7

Combined Administration of Increasing Amounts of Alpha IFN With and without CD40 Agonistic Antibody In the experiment contained in FIG. 7, mice were injected as in the foregoing example, but with increasing amounts of type 1 interferon and in the presence and absence of the agonistic CD40 antibody. The data in the Figure is expressed as the average CD70 MFI between two individual mice and the error bars represent standard deviation. These results similarly reveal that the combined administration of the type 1 interferon and the CD40 agonist increased CD70 expression on DCs in vivo whereas the type 1 interferon and the CD40 agonist, when each were administered in the absence of the other did not.

EXAMPLE 8

Percentage of Antigen specific T cells in Mice Immunized with Decreasing Doses of IFN alpha and CD40 Agonist or Anti-CD70

In this experiment contained in FIG. 8, mice were immunized with anti-CD40 antibody, IFN alpha and anti-CD40 antibody at different decreasing doses as set forth therein, polyIC and CD40 antibody, and alpha interferon and anti-CD40 antibody. It can be seen from the data contained therein that the number of antigen (ovalbumin) specific T cells decreased exponentially with the lower IFN alpha dosages and that number of antigen specific cells with the IFN/polyIC and IFNalpha/CD40 agonist were substantially the same. (See FIG. 8) Thus, the data in FIGS. 6 and 7 and 8 shows that exogenously added IFNα can synergize with anti-CD40 and upregulate CD70 expression on DCs and result in the expansion of antigen specific T cells.

EXAMPLE 9

CD70 Expression on DCs From IFNalphabetaR KO Mice With TLR/CD40 Agonist Combination In order to substantiate that the results seen in FIGS. 6 and 7 with exogenously added IFN alpha correlate to endogenous IFN, experiments were conducted in IFNαβ R mice as depicted in FIG. 9. As shown therein, experiments are performed wherein mice were successfully reconstituted with the transferred bone marrow (in this case, BM expressing GFP +/− Bcl-2, (FIG. 9) and which generated an immune response following immunization 8 weeks after reconstitution (not shown).

As shown in the experiment in FIG. 9, combined TLR/CD40 agonist administration challenge induces CD70 expression only on DCs expressing the targeted TLR in IFNalphabetaR KO mice. In the experiment, IFNalphabetaR mice were injected with anti-CD40 antibody alone, or in combination with polyIC or Pam3Cys. Pam3Cys is a TLR2 agonist and polyIC is a TLR3 agonist. 24 hours later, the spleen DCs were isolated and stained for CD70 expression as afore-described. CD8+ DCs express TLR2 and TLR3, whereas CD11b+DCs express TLR2 but not TLR3. These data suggest that in the absence of IFNalphabeta signaling only DCs stimulated directly through both TLR and CD40 are capable of increased CD70 expression.

This data in combination with the prior data further suggest that this increase in CD70 expression is involved in the concomitant expansion of CD8+ T cells.

EXAMPLE 10

Effect of Type 1 IFN/CD40 Combination Versus Effect of IL-2/CD40 Agonist Combination on Antigen Specific T Cell Numbers This experiment in FIG. 10 was designed to compare the effect of IL-2 another cytokine and a type 1 interferon when combined with a CD40 agonist. As noted above, the synergy achieved with the IFNalpha/CD40 agonist combination is believed to be truly unexpected and is not seen with other cytokine/CD40 agonist combinations.

In this experiment the effect of type 1 IFN/CD40 antibody, IL-2/CD40 antibody, IL-2 alone, IFNalpha alone, and CD40 agonist alone were compared. This results contained in FIG. 10 reveal that IL-2 and IFN/CD40 combinations do not yield similar effects on the percentages of antigen-specific T cell immune cells. Therein, mice were injected with ovalbumin (300 mg) in combination with anti-CD40 (50 mg) recombinant IFN alpha ($1 \times 10^6$ U), IL-2 ($1 \times 10^6$ U) IL-2 and CD40, or the same dosages of IFN and CD40 agonist alone. Seven days later peripheral blood was taken and stained with Kb/ova tetramer to identify the percentage of antigen specific T cells. Numbers in the dot plots are the percent of total CD8+ T cells in the indicated oval gate (tetramer+). The bar graph is the average and standard deviation of 2 mice per injection. The results therein show that the number of antigen specific T cells was much higher in the animals administered the IFN/CD40 combination versus the IL-2/CD40 combination, with the same amount of CD40 agonist and when both cytokines were administered at the same activity levels. This further substantiates that the synergy achieved with the IFN/CD40 agonist combination is unexpected.

EXAMPLE 11

Effect of IFNalpha and CD40 Agonist on Survival Time in Metastatic Melanoma

In this experiment C57Bl/6 mice were intravenously inoculated with 100,000 B16.F10 melanoma cells on day zero. Four days later, mice received 100 micrograms tumor peptide (deltaV) 100 micrograms of anti-CD40 and $1 \times 10^6$ units of alpha interferon. As shown therein the mice which were administered the anti-CD40/IFN combination had a substantially greater survival time. This data further supports the potential application of the subject adjuvant combination in tumor vaccines and cancer therapy.

EXAMPLE 12

Effect of CD40 Agonist/IFNalpha Combination on Metastatic Lung Cancer t

The experiment in FIG. 12 shows that the subject CD40 agonist/IFN alpha combination protects mice from metastatic lung cancer. In this experiment C57Bl/6 mice were intravenously inoculated with 100,000 B16.F10 melanoma cells on day zero. Four days later, mice received 100 micrograms of tumor peptide, deltaV, 100 micrograms anti-CD40 antibody, 100 micrograms of S-27609 (TLR7 agonist) and $1 \times 10^6$ units of alpha interferon. Twenty-one days later post tumor challenge mice were sacrificed, lungs were removed therefrom, and metastatic nodules were counted via a dissection microscope. In Panel A of the Figure is shown digital pictures of representative lungs at day of lung harvest. In panel B is shown an enumeration of lung metastases wherein N=7-8 mice per group. These results show the protective effect of the CD40 agonist/IFN alpha combination versus the other treatments.

EXAMPLE 13

Tumor Infiltrating Analysis from Tumor Bearing Lungs

Experiments shown in FIG. 13 were conducted wherein TIL (tumor infiltrating lymphocytes) analysis from tumor bearing lungs was effected. C57Bl/6 mice were intravenously inoculated with 100.000 B16.F10 melanoma cells on day zero. Five days later, mice received 100 micrograms tumor peptide (deltaV), 100 micrograms anti-CD40 and 1×10$^6$ units of interferon alpha as shown therein. Twenty days post tumor challenge mice were sacrificed. The lungs were removed and TILs were isolated via Percoll gradient centrifugation. Cells were subsequently subjected to flow cytometric analysis to investigate the relative and absolute numbers of infiltrating CD4 (13A and 13D), CD8 (13B and 13E) and FoxP3+ cells (13 C and 13F). In the experiment N=4 mice per group.

EXAMPLE 14

Effect of Combination Immunotherapy on CD8+ T cells That Infiltrate Lungs in Tumor Bearing Mice In this experiment contained in FIG. 14, the effect of the subject combination immunotherapy on the generation of antigen-specific effector CD8+ T cells that infiltrate lungs of tumor bearing mice was analyzed. In the experiment therein C57Bl/6 mice were intravenously inoculated with 100,000 B16.F10 melanoma cells on day zero. Five days later, three mice received 100 micrograms of the tumor peptide (deltaV), 100 micrograms of anti-CD40, and 1×106 units of alpha interferon as indicated. Twenty days post tumor challenge mice were sacrifice and lunges were removed and the TILs were again isolated via Percoll gradient centrifugation. Cells were subsequently stimulated with 1 microgram/mL rhIL-2 and brefeldin A for 12-18 hours and then subjected to intracellular cytokine staining. Cells were first labeled with antibodies to CD8 and CD44, then fixed and rendered permeable before staining with IFNg. Positive cells were calculated by subtracting the background observed with the irrelevant (SIINFEKL) peptide control and then plotted as either percent positive (14A) or absolute numbers (14B) of CD8+ CD44+ IFNg+ T cells. In the experiment N=4 mice per group.

The results in the Figure reveal that the number of antigen specific CD8+ T cells is increased as a result of the subject IFN/CD40 agonist combination administration. These results further substantiate the efficacy of the subject adjuvant combination in cancer vaccines and other therapies wherein such immune potentiation is desired.

As a final note, in order to further describe the invention, this application contains FIG. 15 which contains the sequence of an exemplary agonistic antibody which was used in the examples as well as FIGS. 16 and 17 which depict schematically methods and materials suitable for producing DNA constructs and polypeptide conjugates according to the invention, e.g., using a baculovirus expression system.

It is to be understood that the invention is not limited to the embodiments listed hereinabove and the right is reserved to the illustrated embodiments and all modifications coming within the scope of the following claims.

The various references to journals, patents, and other publications which are cited herein comprise the state of the art and are incorporated by reference as though fully set forth.

The invention claimed is:

1. An immunostimulatory regimen for inducing CD70 expression on dendritic cells and inducing the expansion of CD8+ T cells in a subject in need thereof and thereby eliciting an anti-infectious immune response comprising administering type 1 interferon and an immune agonist polypeptide other than said type I interferon, and further including the administration of an infectious agent antigen, wherein said regimen does not include the administration of a TLR agonist and further requires that the only immune agonist polypeptide other than said type 1 interferon administered in said immunostimulatory regimen consists of an agonistic CD40L polypeptide or a CD40 agonistic antibody or a CD40 agonistic antibody fragment polypeptide, and further wherein said agonistic CD40L polypeptide, CD40 agonistic antibody or CD40 agonistic antibody fragment and said type 1 interferons are administered in amounts that in combination, but not separately, result in the induction of CD70 expression on dendritic cells.

2. An immunostimulatory regimen for inducing the expansion of CD8+ T cells in a subject in need thereof and eliciting an anti-infectious agent immune response by administering a type 1 interferon and an immune agonist polypeptide other than said type 1 interferon and further including the administration of an infectious antigen, wherein said regimen does not include the administration of a TLR agonist and further requires that the only immune agonist polypeptide administered in said immunostimulatory regimen other than said type 1 interferon consists of a an agonistic CD40L polypeptide or CD40 agonistic antibody or a CD40 agonistic antibody fragment polypeptide and wherein said an agonistic CD40L polypeptide, CD40 agonistic antibody or CD40 agonistic antibody fragment and said type 1 interferon are administered in amounts that in combination, but not separately, result in the expansion of CD8+ T cells.

3. An immunostimulatory therapeutic regimen for inducing primary and memory T cell responses in a subject in need thereof and eliciting an anti-infectious agent immune response by administering type 1 interferon and an immune agonist polypeptide other than said type 1 interferon and another further including an infectious agent antigen, wherein said regimen does not include the administration of a TLR agonist and further requires that the only immune agonist polypeptide used in said immunostimulatory regimen other than said type 1 interferon consists of a an agonistic CD40L polypeptide or CD40 agonistic antibody or a CD40 agonistic antibody fragment polypeptide and wherein said an agonistic CD40L polypeptide, CD40 agonistic antibody or CD40 agonistic antibody fragment and said type interferon are administered in amounts that in combination, but not separately, result in a synergistic effect on immunity resulting in enhanced primary and memory CD8+ T cell responses specific to the infectious agent.

4. The immunostimulatory regimen of claim 1 wherein the an agonistic CD40L polypeptide or CD40 agonistic antibody or antibody fragment, type 1 interferon are administered as discrete entities.

5. The immunostimulatory regimen of claim 2 wherein the an agonistic CD40L polypeptide or CD40 agonistic antibody or antibody fragment, type 1 interferon are administered as discrete entities.

6. The immunostimulatory regimen of claim 3 wherein the an agonistic CD40L polypeptide or CD40 agonistic antibody or antibody fragment, type 1 interferon and infectious agent antigen are administered as discrete entities.

7. The immunostimulatory regimen of claim 1 wherein the an agonistic CD40L polypeptide or CD40 agonistic antibody or antibody fragment, type 1 interferon and infectious agent antigen are administered as discrete entities in combination.

8. The immunostimulatory regimen of claim 3 wherein the agonistic CD40L polypeptide or CD40 agonistic antibody or antibody fragment, type 1 interferon and infectious agent antigen are administered as discrete entities in combination.

9. The immunostimulatory regimen of claim 3 wherein the an agonistic CD40L polypeptide or CD40 agonistic antibody or antibody fragment, type 1 interferon are administered as discrete entities in combination.

10. The immunostimulatory regimen of claim 1 wherein the agonistic CD40L polypeptide or CD40 agonistic antibody or antibody fragment, type 1 interferon and infectious antigen are separately administered as discrete entities.

11. The immunostimulatory regimen of claim 2 wherein the an agonistic CD40L polypeptide or CD40 agonistic antibody or antibody fragment, type 1 interferon and infectious antigen are separately administered as discrete entities.

12. The immunostimulatory regimen of claim 3 wherein the an agonistic CD40L polypeptide or CD40 agonistic antibody or antibody fragment, type 1 interferon and infectious antigen are separately administered as discrete polypeptides entities in combination.

13. The immunostimulatory regimen of claim 1 wherein the type 1 interferon is an alpha or beta interferon.

14. The immunostimulatory regimen of claim 2 wherein the type 1 interferon is an alpha or beta interferon.

15. The immunostimulatory regimen of claim 3 wherein the type 1 interferon is an alpha or beta interferon.

16. The immunostimulatory regimen of claim 1 wherein the type 1 interferon is a human alpha or beta interferon.

17. The immunostimulatory regimen of claim 2 wherein the type 1 interferon is a human alpha or beta interferon.

18. The immunostimulatory regimen of claim 3 wherein the type 1 interferon is a human alpha or beta interferon.

19. The immunostimulatory regimen of claim 1 wherein the type 1 interferon is PEGylated.

20. The immunostimulatory regimen of claim 2 wherein the type 1 interferon is PEGylated.

21. The immunostimulatory regimen of claim 3 wherein the type 1 interferon is PEGylated.

22. The immunostimulatory regimen of claim 1 wherein the CD40 agonistic antibody or fragment is an agonistic chimeric, human, or humanized anti-CD40 antibody or an agonistic CD40 antibody fragment which is selected from a Fab, F(ab')$_2$, Fd, and a Fv.

23. The immunostimulatory regimen of claim 2 wherein the CD40 agonist is an agonistic chimeric, human, or humanized anti-CD40 antibody or an agonistic CD40 antibody fragment which is selected from a Fab, F(ab')$_2$, Fd, and a Fv.

24. The immunostimulatory regimen of claim 3 wherein the CD40 agonist is an agonistic chimeric, human, or humanized anti-CD40 antibody or an agonistic CD40 antibody fragment which is selected from a Fab, F(ab')$_2$, Fd, and a Fv.

25. The immunostimulatory regimen of claim 1 wherein said type 1 interferon is selected from alpha interferon, beta interferon, omega interferon, tau interferon, zeta interferon and epsilon interferon.

26. The immunostimulatory regimen of claim 2 wherein said type 1 interferon is selected from alpha interferon, beta interferon, omega interferon, tau interferon, zeta interferon and epsilon interferon.

27. The immunostimulatory regimen of claim 3 wherein said type 1 interferon is selected from alpha interferon, beta interferon, omega interferon, tau interferon, zeta interferon and epsilon interferon.

28. The immunostimulatory regimen of claim 1 wherein the an agonistic CD40L polypeptide or agonistic CD40 antibody or antibody fragment and the type 1 interferon are administered within 24 hours of each other.

29. The immunostimulatory regimen of claim 2 wherein the an agonistic CD40L polypeptide or agonistic CD40 antibody or antibody fragment and the type 1 interferon are administered within 24 hours of each other.

30. The immunostimulatory regimen of claim 3 wherein the an agonistic CD40L polypeptide or agonistic CD40 antibody or antibody fragment and the type 1 interferon are administered within 24 hours of each other.

31. The immunostimulatory regimen of claim 1 wherein the an agonistic CD40L polypeptide or agonistic CD40 antibody or antibody fragment and the type 1 interferon are administered within 1-8 hours of each other.

32. The immunostimulatory regimen of claim 2 wherein the an agonistic CD40L polypeptide or agonistic CD40 antibody or antibody fragment and the type 1 interferon are administered within 1-8 hours of each other.

33. The immunostimulatory regimen of claim 3 wherein the an agonistic CD40L polypeptide or agonistic CD40 antibody or antibody fragment and the type 1 interferon are administered within 1-8 hours of each other.

34. The immunostimulatory regimen of claim 1 wherein the an agonistic CD40L polypeptide or CD40 agonistic antibody or antibody fragment and the type 1 interferon are administered at the same time.

35. The immunostimulatory regimen of claim 2 wherein the an agonistic CD40L polypeptide or CD40 agonistic antibody or fragment and the type I interferon are administered at the same time.

36. The immunostimulatory regimen of claim 3 wherein the an agonistic CD40L polypeptide or CD40 agonistic antibody or antibody fragment and the type 1 interferon are administered at the same time.

37. The regimen of claim 1 wherein the infectious agent is a bacterium, virus, fungus, mycoplasm, or parasite.

38. The regimen of claim 2 wherein the infectious agent is a bacterium, virus, fungus, mycoplasm, or parasite.

39. The regimen of claim 3 wherein infectious agent is a bacterium, virus, fungus, mycoplasm, or parasite.

40. The regimen of claim 1 wherein the infectious agent is a gram positive or gram negative bacterium.

41. The regimen of claim 2 wherein the infectious agent is a gram positive or gram negative bacterium.

42. The regimen of claim 3 wherein the infectious agent is a gram positive or gram negative bacterium.

43. The immunostimulatory regimen of claim 1 wherein the infectious agent is a gram positive or gram negative bacterium selected from a *Pasteurella* species, *Staphylococci* species, *Streptococci* species, *Escherichia coli*, *Pseudomonas* species, *Salmonella* species, *Heliobacter pyloris*, *Borrelia burgdorferi*, *Legionella pneumophilia*, *Mycobacteria* spp. selected from *M. tuberculosis, M. avium, M. intracellilare, M. kansaii*, and *M. gordonae*), *Staphylococcus aureus, Neisseria gonorrhoeae, Neisseria meningitidis, Listeria monocytogeners, Streptococcus pyogenes*, (group A *Streptococcus*), *Streptococcus agalactiae*(Group B *Streptococcus*), *Streptococcus* (viridans group), *Streptococcus faecalis, Streptococcus bovis, Streptococcus* (aenorobic spp.), *Streptococcus pneumoniae*, pathogenic *Campylobacter* spp., *Enterococcus* spp., *Haemophilus influenzae, Bacillus anthracis, Corynebacterium diptheriae, Corynebacterium* spp., *Erysipelothrix rhusiopathie, Clostridium perfringens, Clostridium tetani, Enterobacter aerogenes, Klebsiella pneumoniae, Pasteurella multocida, Bacteroides* spp., *Fusobacterium nucleatum, Streptobacillus moniliformis, Treponema pallidum, Treponema pertenue, Leptospira, Rickettsia*, and *Actinomyces israelii*.

44. The immunostimulatory regimen of claim 2 wherein the infectious agent is a gram positive or gram negative bacterium selected from a *Pasteurella* species, *Staphylococci* species, *Streptococci* species, *Escherichia coli*, *Pseudomonas* species, *Salmonella* species, *Heliobacter pyloris*, *Borrelia burgdorferi*, *Legionella pneumophilia*, *Mycobacteria* spp. selected from *M. tuberculosis, M. avium, M. intracellilare, M. kansaii*, and *M. gordonae*), *Staphylococcus aureus, Neisseria gonorrhoeae, Neisseria meningitidis, Listeria* monocytogeners, *Streptococcus pyogenes*, (group A *Streptococcus*), *Streptococcus agalactiae*(Group B *Streptococcus*), *Streptococcus* (viridans group), *Streptococcus faecalis, Streptococcus bovis, Streptococcus* (aenorobic spp.), *Streptococcus pneumoniae*, pathogenic *Campylobacter* spp., *Enterococcus* spp., *Haemophilus influenzae, Bacillus anthracis, Corynebacterium diptheriae, Corynebacterium* spp., *Erysipelothrix rhusiopathie, Clostridium perfringens, Clostridium tetani, Enterobacter aerogenes, Klebsiella pneumoniae, Pasteurella multocida, Bacteroides* spp., *Fusobacterium nucleatum, Streptobacillus moniliformis, Treponema pallidum, Treponema pertenue, Leptospira, Rickettsia*, and *Actinomyces israelii*.

45. The immunostimulatory regimen of claim 3 wherein the infectious agent is a gram positive or gram negative bacterium selected from a *Pasteurella* species, *Staphylococci* species, *Streptococci* species, *Escherichia coli*, *Pseudomonas* species, *Salmonella* species, *Heliobacter pyloris*, *Borrelia burgdorferi*, *Legionella pneumophilia*, *Mycobacteria* spp. selected from *M. tuberculosis, M. avium, M. intracellilare, M. kansaii*, and *M. gordonae*), *Staphylococcus aureus, Neisseria gonorrhoeae, Neisseria meningitidis, Listeria monocytogeners, Streptococcus pyogenes*, (group A *Streptococcus*), *Streptococcus agalactiae*(Group B *Streptococcus*), *Strepto-*

*coccus* (viridans group), *Streptococcus faecalis, Streptococcus bovis, Streptococcus* (aenorobic spp.), *Streptococcus pneumoniae, pathogenic Campylobacter* spp., *Enterococcus* spp., *Haemophilus influenzae, Bacillus anthracis, Corynebacterium diptheriae, Corynebacterium* spp., *Erysipelothrix rhusiopathie, Clostridium perfringens, Clostridium tetani, Enterobacter aerogenes, Klebsiella pneumoniae, Pasteurella multocida, Bacteroides* spp., *Fusobacterium nucleatum, Streptobacillus moniliformis, Treponema pallidum, Treponema pertenue, Leptospira, Rickettsia,* and *Actinomyces israelii*.

46. The immunostimulatory regimen of claim 1 wherein the infectious agent is a fungus or mycoplasm.

47. The immunostimulatory regimen of claim 2 wherein the infectious agent is a fungus or mycoplasm.

48. The immunostimulatory regimen of claim 3 wherein the infectious agent is a fungus or mycoplasm.

49. The immunostimulatory regimen of claim 1 wherein the infectious agent is a fungus selected from *Coccidoides immitis, Cryptococcus neoformans, Candida albicans Blastomyces dermatidis, Histoplasma capsulatum, Chlamydia trachomatis, Nocardia* spp., and *Pneumocytis carinii*.

50. The immunostimulatory regimen of claim 2 wherein the infectious agent is a fungus fungus selected from *Coccidoides immitis, Cryptococcus neoformans, Candida albicans Blastomyces dermatidis, Histoplasma capsulatum, Chlamydia trachomatis, Nocardia* spp., and *Pneumocytis carinii*.

51. The immunostimulatory regimen of claim 3 wherein the infectious agent is a fungus fungus selected from *Coccidoides immitis, Cryptococcus neoformans, Candida albicans Blastomyces dermatidis, Histoplasma capsulatum, Chlamydia trachomatis, Nocardia* spp., and *Pneumocytis carinii*.

52. The immunostimulatory regimen of claim 1 wherein the CD40 agonistic antibody or antibody fragment, the type 1 interferon and the infectious antigen are comprised in the same or different compositions.

53. The immunostimulatory regimen of claim 2 wherein the CD40 agonistic antibody or antibody fragment, the type 1 interferon and the infectious antigen are comprised in the same or different compositions.

54. The immunostimulatory regimen of claim 3 wherein the CD40 agonistic antibody or antibody fragment, the type 1 interferon and the infectious antigen are comprised in the same or different compositions.

55. The immunostimulatory regimen of claim 1 wherein the CD40 agonistic antibody or antibody fragment, the type 1 interferon and the infectious antigen are comprised in the same or different compositions.

56. The immunostimulatory regimen of claim 2 wherein the CD40 agonistic antibody or antibody fragment, the type 1 interferon and the infectious antigen are comprised in the same or different compositions.

57. The immunostimulatory regimen of claim 3 wherein the CD40 agonistic antibody or antibody fragment, the type 1 interferon and the infectious antigen are comprised in the same or different compositions.

58. The immunostimulatory regimen of claim 1 wherein the CD40 agonistic antibody or antibody fragment, the type 1 interferon and the infectious antigen are comprised in the same or different compositions.

59. The immunostimulatory regimen of claim 2 wherein the CD40 agonistic antibody or antibody fragment, the type 1 interferon and the infectious antigen are comprised in the same or different compositions.

60. The immunostimulatory regimen of claim 3 wherein the CD40 agonistic antibody or antibody fragment, the type 1 interferon and the infectious antigen are comprised in the same or different compositions.

61. The immunostimulatory regimen of claim 1 which is effected in a patient with an infectious disorder.

62. The immunostimulatory regimen of claim 2 which is effected in a patient with an infectious disorder.

63. The immunostimulatory regimen of claim 3 which is effected in a patient with an infectious disorder.

64. The immunostimulatory regimen of claim 1 wherein the CD40L, CD40 agonistic antibody or antibody fragment, the type 1 interferon and the infectious antigen are administered mucosally, topically, orally, intravenously, intramuscularly, intranasally, vaginally, rectally, intratumorally, intrathecally, or intraocularly.

65. The immunostimulatory regimen of claim 2 wherein the CD40L, CD40 agonistic antibody or antibody fragment, the type 1 interferon and the infectious antigen are administered mucosally, topically, orally, intravenously, intramuscularly, intranasally, vaginally, rectally, intratumorally, intrathecally, or intraocularly.

66. The immunostimulatory regimen of claim 3 wherein the CD40L, CD40 agonistic antibody or antibody fragment, the type 1 interferon and the infectious antigen are administered mucosally, topically, orally, intravenously, intramuscularly, intranasally, vaginally, rectally, intratumorally, intrathecally, or intraocularly.

* * * * *